(12) United States Patent
Mack

(10) Patent No.: US 12,168,692 B1
(45) Date of Patent: Dec. 17, 2024

(54) ANTIBODIES TARGETING CCR2

(71) Applicant: GRANITE BIO AG, Basel (CH)

(72) Inventor: Matthias Mack, Regensburg (DE)

(73) Assignee: Granite Bio AG, Basel (CH)

( * ) Notice: Subject to any disclaimer, the term of this patent is extended or adjusted under 35 U.S.C. 154(b) by 0 days.

(21) Appl. No.: 18/793,279

(22) Filed: Aug. 2, 2024

Related U.S. Application Data

(63) Continuation of application No. 18/700,201, filed as application No. PCT/EP2022/079744 on Oct. 25, 2022.

(51) Int. Cl.
    *C07K 16/00*     (2006.01)
    *C07K 16/28*     (2006.01)

(52) U.S. Cl.
    CPC ...... *C07K 16/2866* (2013.01); *C07K 2317/24* (2013.01)

(58) Field of Classification Search
    None
    See application file for complete search history.

(56) References Cited

U.S. PATENT DOCUMENTS 9,068,002 B2 * 6/2015 Prinz ............... A61P 25/00
2011/0274696 A1    11/2011 Gladue et al.

FOREIGN PATENT DOCUMENTS

| | | |
|---|---|---|
| EP | 2727944 A1 | 5/2014 |
| WO | WO-2007115713 A1 | 10/2007 |
| WO | WO-2010021697 A2 | 2/2010 |
| WO | WO-2013192596 A2 | 12/2013 |
| WO | WO-2016079276 A1 | 5/2016 |

OTHER PUBLICATIONS

U.S. Appl. No. 18/700,201, filed Apr. 10, 2024, Matthias Mack.
PCT/EP2022/079744, Oct. 25, 2022, Matthias Mack.
International Search Report and Written Opinion received for PCT/EP2022/079744, mailed Feb. 21, 2023.

* cited by examiner

*Primary Examiner* — Meera Natarajan
(74) *Attorney, Agent, or Firm* — Dechert LLP; Andrew T. Wilkins; Sharla F. Flohr

(57) ABSTRACT

The present disclosure relates to antibodies and antibody fragment that are specific for CCR2. The antibodies deplete CCR2-positive cells and block MCP-1 (CCL2) induced downregulation of CCR2 on human leukocytes. Furthermore, they possess advantageous biophysical properties. The antibodies are useful for the treatment of inflammatory diseases, autoimmune diseases, hematologic malignancies and potentially other illnesses.

30 Claims, 19 Drawing Sheets
Specification includes a Sequence Listing.

ANTIBODIES TARGETING CCR2

RELATED APPLICATIONS

This application is a continuation application of U.S. patent application Ser. No. 18/700,201, filed Apr. 10, 2024, which is a U.S. National Phase application, filed under 35 U.S.C. § 371, of International Application No. PCT/EP2022/079744, filed Oct. 25, 2022, which claims benefit of, and priority to EP 21204904.3, filed on Oct. 27, 2021, the entire contents of which are incorporated herein by reference.

SEQUENCE LISTING

The instant application contains a Sequence Listing which has been submitted electronically in XML format and is hereby incorporated by reference in its entirety. Said XML copy, created on Feb. 8, 2024, is named BHIP-C08-01-PCT_Seq listing and is 28,835 bytes in size.

FIELD OF THE INVENTION

The present disclosure relates to antibodies and antibody fragment that are specific for CCR2. The antibodies deplete CCR2-positive cells and block MCP-1 (CCL2) induced downregulation of CCR2 on human leukocytes. Furthermore, they possess advantageous biophysical properties. The antibodies are useful for the treatment of inflammatory diseases, autoimmune diseases, hematologic malignancies and potentially other illnesses.

BACKGROUND

Monocytes migrate to sites of inflammation under the influence of chemokines and cytokines. One such chemokine is MCP-1 that binds to the chemokine receptor CCR2, which causes monocyte to egress from the bone marrow. MCP-1, which is secreted by cells during inflammatory diseases, autoimmune diseases, hematologic malignancies and other illnesses.

Several molecules targeting the MCP-1/CCR2 pathway were or are still tested and some showed promising results, but none was approved so far. Most of the drugs developed are small organic molecules. For example cenicriviroc, a small molecule developed by Takeda and Tobira Therapeutics, is currently in Phase 3 clinical testing. Cenicriviroc is however not specific for CCR2, but also inhibits CCR5.

STI-B0201 is an antibody generated by Sorrento, but no clinical development is reported. Anti-CCR2 antibodies of Sorrento are disclosed in WO2013/192596. Unlike the antibodies of the present disclosure, the antibodies of WO2013/192596 do cross react with mouse CCR2. Antibodies of Anti-CCR2 antibodies are also disclosed in WO2007/115713 and U.S. Pat. No. 9,068,002. These are however murine antibodies which, likewise, never were developed. MLNM1202 (plozalizumab) is another anti-CCR2 antibody, but development was discontinued by Millennium. Antibodies of Takeda/Millennium are disclosed in WO2016/079276. Antibodies of Amgen are disclosed in US2011/0274696. The antibodies of US2011/0274696 show reactivity to cynomolgus CCR2, whereas the antibodies of the present disclosure do not cross react with cynomolgus CCR2. The antibodies of the present disclosure however do cross react with marmoset CCR2. Antibodies against CCR2 of the University of Regensburg/Yeda/Tel Aviv Medical Center are disclosed in U.S. Pat. No. 9,068,002. Antibodies against CCR2 of Pfizer are disclosed in WO2010021697. Yet again, no development is reported.

Hence, whilst there is a need and a great interest in developing specific anti-CCR2 targeting moieties, there is currently no anti-CCR2 antibody in advanced development. The present invention discloses novel antibodies that are highly specific for CCR2, have a high affinity and biophysical properties that are beneficial for successful clinical development.

SUMMARY OF THE INVENTION

The present disclosure relates to novel antibodies and antibody fragments that are specific for human CCR2. The antibodies are cross-reactive to marmoset CCR2, a relevant animal model for clinical development. Compared to the antibodies in the prior art, the antibodies and antibody fragments of the present disclosure have several advantages. One advantage is the high affinity to the target antigen. The affinity of the antibodies and antibody fragments of the present invention is at least one magnitude higher than that of any prior art antibody. Furthermore, the antibodies and antibody fragments of the present disclosure have superior biophysical properties. This includes a high temperature stability, a high stability upon repeated freezing and thawing, a stability over a broad pH range, and a high stability in human plasma. The developability of the antibodies is therefore highly increased. The stability of the binders also leads to prolonged serum levels of the antibodies, which makes it possible to administer the antibodies at lower doses, thereby reducing potential side effects.

The present disclosure relates to antibodies and antibody fragments specific for human CCR2 which block MCP-1 induced downregulation of CCR2 on human leukocytes.

The present disclosure also relates to antibodies and antibody fragments specific for human CCR2 which bind to the ECL-2 domain (SEQ ID NO: 2) of human CCR2.

The present disclosure also relates to antibodies and antibody fragments specific for human CCR2 which do not bind to human CCR5 (SEQ ID NO: 6).

The present disclosure also relates to antibodies and antibody fragments specific for human CCR2 which are cross-reactive with marmoset CCR2.

The present disclosure also relates to antibodies and antibody fragments specific for human CCR2 which have an at least 10-fold higher affinity to human CCR2 than antibody DOC2. The present disclosure also relates to antibodies and antibody fragments wherein said antibody or antibody fragment has a higher affinity to human CCR2 expressed on human monocytes than an antibody comprising a variable heavy chain of SEQ ID No. 28 and a variable heavy chain of SEQ ID No. 29. Preferably said antibody or antibody fragment has an at least 2-fold, an at least 3-fold, an at least 5-fold or an at least 10-fold higher affinity at an antibody concentration between 0.1-1.0 µg/ml.

Preferred antibodies and antibody fragments of the present disclosure are of the human IgG class. Even more preferred antibodies or antibody fragment of the present disclosure are of the IgG1 class.

Preferred antibodies and antibody fragments of the present disclosure are monoclonal antibodies or antibody fragments.

Preferred antibodies and antibody fragments of the present disclosure are humanized antibodies or antibody fragments.

The present disclosure also relates to antibodies and antibody fragments specific for human CCR2 which have superior biophysical properties. This includes a high temperature stability, a high stability upon repeated freezing and thawing, a stability over a broad pH range, and a high stability in human plasma.

Preferred antibodies and antibody fragments of the present disclosure comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

Preferred antibodies and antibody fragments of the present disclosure comprises the variable heavy chain of SEQ ID NO: 22 and the variable light chain of SEQ ID NO 23.

The present disclosure also relates to nucleic acid composition comprising a nucleic acid sequence or a plurality of nucleic acid sequences encoding antibodies or antibody fragments comprising the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

The present disclosure relates to nucleic acid composition comprising a nucleic acid sequence or a plurality of nucleic acid sequences encoding antibodies or antibody fragments comprising the variable heavy chain of SEQ ID NO: 22 and the variable light chain of SEQ ID NO 23.

The present disclosure also relates to vectors comprising such nucleic acids or nucleic acid compositions.

The present disclosure also relates to host cells comprising such nucleic acids, nucleic acid compositions or vectors.

The antibodies and antibody fragment of the present disclosure are for use in medicine. Preferred are the antibodies and antibody fragment of the present disclosure for use in the treatment of inflammatory diseases, autoimmune diseases, hematologic malignancies and potentially other diseases.

The present disclosure also relates to pharmaceutical composition comprising the antibodies and antibody fragments of the present disclosure and a pharmaceutically acceptable

DETAILED DESCRIPTION

Figure 1:
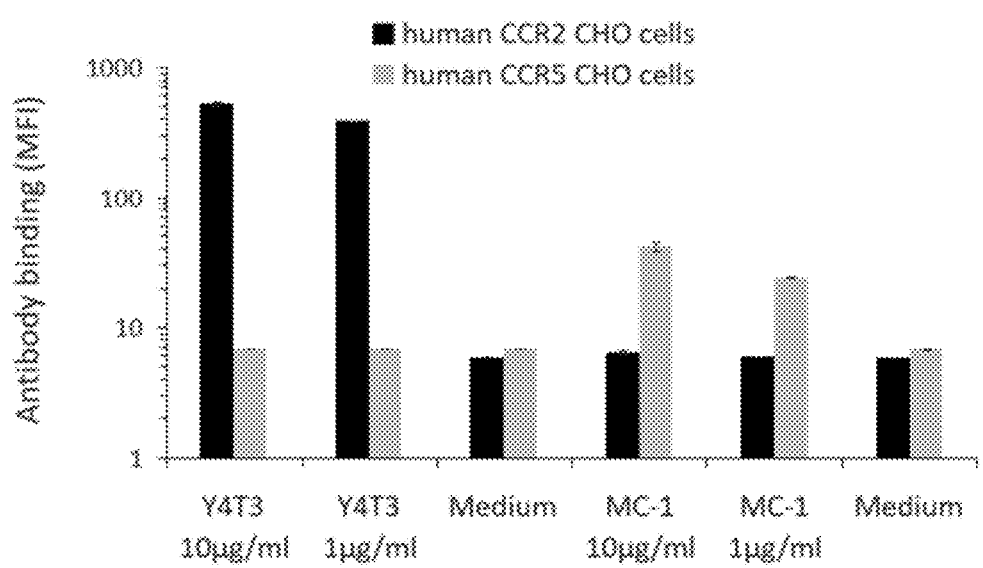
FIG. 1 shows the specific binding of the antibodies of the present invention to human CCR2. No binding to human CCR5 was observed. Anti-CCR5 antibody MC-1 was specific for human CCR5, but did not show any binding to human CCR2.

The disclosure pertains to antibodies, which specifically bind to CCR2.

Definitions

The term "CCR2" refers to a protein known as C-C Motif Chemokine Receptor 2, also known as CD192 or MCP-1 receptor. Human CCR2 exists in two main isoforms, CCR2a and CCR2b, which are produced by alternative splicing. CCR2a and CCR2b only differ at the cytosolic, C-terminal part. The extracellular part which is accessible to therapeutic antibodies and antibody fragments is identical in both isoforms.

Human CCR2b has the amino acid sequence of (UniProtKB/Swiss-Prot: P41597):

(SEQ ID NO: 1)
MLSTSRSRFIRNTNESGEEVTTFFDYDYGAPCHKFDVKQIGAQLLPPLY

SLVFIFGFVGNMLVVLILINCKKLKCLTDIYLLNLAISDLLFLITLPLW

AHSAANEWVFGNAMCKLFTGLYHIGYFGGIFFIILLTIDRYLAIVHAVF

ALKARTVTFGVVTSVITWLVAVFASVPGIIFTKCQKEDSVYVCGPYFPR

GWNNFHTIMRNILGLVLPLLIMVICYSGILKTLLRCNEKKRHRAVRVI

FTIMIVYFLFWTPYNIVILLNTFQEFFGLSNCESTSQLDQATQVTETLG

MTHCCINPIIYAFVGEKFRRYLSVFFRKHITKRFCKQCPVFYRETVDGV

TSTNTPSTGEQEVSAGL

The extracellular domain 2 (ECL2) of human CCR2 has the amino acid sequence of (SEQ ID NO: 2)
TKCQKEDSVYVCGPYFPRGWNNFHTIMR Marmoset monkey (*Callithrix jacchus*) CCR2b has the amino acid sequence of (SEQ ID NO: 3)
MLSTSHSRFIRNTESGEEVTTIFDYDYGAPCHKFDVKQIGAQLLPPLYS

LVFIFGFVGNMLVVLILINCKKLKSLTDIYLLNLAVSDLLFLITLPLWA

HSAANEWVFGNAVCKLFTGLYHIGYFGGIFFIILLTIDRYLAIVHAVFA

LKARTVTFGVVTSVITWFVAVFASVPGIIFTKSQKEDSVYVCGPYFPRG

WNHFHTIMRNLLGLVLPLLVMIICYSGILKTLLRCRNEKKRHRAVRLIF

TIMIVYFLFWTPYNIVVLLNTFQEFFGLSNCESTSQLDQATQVTETLGM

THCCINPIIYAFVGEKFRRYLSVFFRKHIAKRFCKQCPVFYRETVDGVT

STNTPSTGEQEVSAGL

Rhesus monkey (*Macaca mulatta*) CCR2b has the amino acid sequence of (SEQ ID NO: 4)
MLSTSRSRFIRNINGSGEEVTTFFDYDYGAPCHKFDVKQIGAQLLPPLY

SLVFIFGFVGNMLVVLILINCKKLKSLTDIYLLNLAISDLLFLITLPLW

AHSAANEWVFGNAMCKLFTGLYHIGYLGGIFFIILLTIDRYLAIVHAVF

ALKARTVTFGVVTSVITWLVAVFASVPGIIFTKCQEEDSVYICGPYFPR

GWNNFHTIMRNILGLVLPLLIMVICYSGILKTLLRCRNEKKRHRAVRLI

FTIMIVYFLFWTPYNIVILLNTFQEFFGLSNCESTRQLDQATQVTETLG

MTHCCINPIIYAFVGEKFRRYLSMFFRKYITKRFCKQCPVFYRETVDGV

TSTNTPSTAEQEVSVGL

CCR2 is the key functional receptor for MCP-1. Its binding to MCP-1 mediates chemotaxis and migration of monocytes and macrophages.

The term "MCP-1" refers to a protein known as Monocyte chemotactic Protein 1. It is also known as CCL2 (C-C Motif Chemokine Ligand 2). Human MCP-1 has the amino acid sequence of (UniProtKB/Swiss-Prot: P13500):

(SEQ ID NO: 5)
MKVSAALLCLLLIAATFIPQGLAQPDAINAPVTCCYNFTNRKISVQRLA

SYRRITSSKCPKEAVIFKTIVAKEICADPKQKWVQDSMDHLDKQTQTPK

T

The term "CCR5" refers to a protein known as C-C Motif Chemokine Receptor 5. It is also known as CD195. Human CCR5 has the amino acid sequence of (UniProtKB/Swiss-Prot: P51681):

(SEQ ID NO: 6)
MDYQVSSPIYDINYYTSEPCQKINVKQIAARLLPPLYSLVFIFGFVGNM

LVILILINCKRLKSMTDIYLLNLAISDLFFLLTVPFWAHYAAAQWDFGN

TMCQLLTGLYFIGFFSGIFFIILLTIDRYLAVVHAVFALKARTVTFGVV

TSVITWVVAVFASLPGIIFTRSQKEGLHYTCSSHFPYSQYQFWKNFQTL

KIVILGLVLPLLVMVICYSGILKTLLRCNEKKRHRAVRLIFTIMIVYF

LFWAPYNIVLLLNTFQEFFGLNNCSSSNRLDQAMQVTETLGMTHCCINP

IIYAFVGEKFRNYLLVFFQKHIAKRFCKCCSIFQQEAPERASSVYTRST

GEQEISVGL

In certain experiments of the present disclosure the following additional constructs were used.

Human CCR2b with the ECL2 domain of rhesus monkey:

(SEQ ID NO: 7)
MLSTSRSRFIRNTNESGEEVTTFFDYDYGAPCHKFDVKQIGAQLLPPLY

SLVFIFGFVGNMLVVLILINCKKLKCLTDIYLLNLAISDLLFLITLPLW

AHSAANEWVFGNAMCKLFTGLYHIGYFGGIFFIILLTIDRYLAIVHAVF

ALKARTVTFGVVTSVITWLVAVFASVPGIIFTKCQEEDSVYICGPYFPR

GWNNFHTIMRNILGLVLPLLIMVICYSGILKTLLRCNEKKRHRAVRVI

FTIMIVYFLFWTPYNIVILLNTFQEFFGLSNCESTSQLDQATQVTETLG

MTHCCINPIIYAFVGEKFRRYLSVFFRKHITKRFCKQCPVFYRETVDGV

TSTNTPSTGEQEVSAGL

The rhesus ECL2 domain differs from the human ECL2 domain in two amino acid residues.

Human CCR2b with the ECL3 domain of rhesus monkey:

(SEQ ID NO: 8)
MLSTSRSRFIRNTNESGEEVTTFFDYDYGAPCHKFDVKQIGAQLLPPLY

SLVFIFGFVGNMLVVLILINCKKLKCLTDIYLLNLAISDLLFLITLPLW

AHSAANEWVFGNAMCKLFTGLYHIGYFGGIFFIILLTIDRYLAIVHAVF

ALKARTVTFGVVTSVITWLVAVFASVPGIIFTKCQKEDSVYVCGPYFPR

GWNNFHTIMRNILGLVLPLLIMVICYSGILKTLLRCNEKKRHRAVRVI

```
FTIMIVYFLFWTPYNIVILLNTFQEFFGLSNCESTRQLDQATQVTETLG

MTHCCINPIIYAFVGEKFRRYLSVFFRKHITKRFCKQCPVFYRETVDGV

TSTNTPSTGEQEVSAGL
```

The rhesus ECL3 domain differs from the human ECL2 domain in one amino acid residue.

Human CCR2b with the N-terminus of rhesus monkey:

```
                                            (SEQ ID NO: 9)
MLSTSRSRFIRNINGSGEEVTTFFDYDYGAPCHKFDVKQIGAQLLPPLY

SLVFIFGFVGNMLVVLILINCKKLKCLTDIYLLNLAISDLLFLITLPLW

AHSAANEWVFGNAMCKLFTGLYHIGYFGGIFFIILLTIDRYLAIVHAVF

ALKARTVTFGVVTSVITWLVAVFASVPGIIFTKCQKEDSVYVCGPYFPR

GWNNFHTIMRNILGLVLPLLIMVICYSGILKTLLRCRNEKKRHRAVRVI

FTIMIVYFLFWTPYNIVILLNTFQEFFGLSNCESTSQLDQATQVTETLG

MTHCCINPIIYAFVGEKFRRYLSVFFRKHITKRFCKQCPVFYRETVDGV

TSTNTPSTGEQEVSAGL
```

The N-terminus of rhesus CCR2 differs from human CCR2 in one amino acid residue.

The term "antibody" as used herein refers to a protein comprising at least two heavy (H) chains and two light (L) chains inter-connected by disulfide bonds, which interacts with an antigen. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., Igd, lgG2, lgG3, lgG4, lgA1 and lgA2) or subclass. Both the light and heavy chains are divided into regions of structural and functional homology.

The term "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1 126-1 136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8: 1057-1062; and U.S. Pat. No. 5,641,870).

The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g. Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5$^{th}$ edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948; Annals of the New York Academy of Sciences, 764, 47-49 (1995); Nucleic Acids Research, 25, 206-211 (1997).

A "human antibody" or "human antibody fragment", as used herein, is an antibody and antibody fragment having variable regions in which both the framework and CDR regions are from sequences of human origin. Human antibodies can also be isolated from synthetic libraries or from transgenic mice (e.g. Xenomouse) provided the respective system yield in antibodies having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86).

A "humanized antibody" or "humanized antibody fragment" is defined herein as an antibody molecule, which has constant antibody regions derived from sequences of human origin and the variable antibody regions or parts thereof or only the CDRs are derived from another species. For example, a humanized antibody can be CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule, which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH, VL, CDR or FR regions) are derived from sequences found in a non-human animal, e.g. a mouse, rat, rabbit or hamster.

The term "isolated antibody" refers to an antibody or antibody fragment that is substantially free of other antibodies or antibody fragments having different antigenic specificities. Moreover, an isolated antibody or antibody fragment may be substantially free of other cellular material and/or chemicals. Thus, in some aspects, antibodies provided are isolated antibodies, which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody", as used herein, includes all antibodies that are prepared, expressed, created or segregated by means not existing in nature. For example, antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody. In an embodiment, the antibodies and antibody fragment disclosed herein are isolated from the HuCAL library (Rothe et al, J. Mol. Biol. (2008) 376, 1 182-1200).

As used herein, an antibody "binds specifically to", "specifically binds to", is "specific to/for" or "specifically recognizes" an antigen, such as human CCR2, if such antibody is able to discriminate between such antigen and one or more reference antigen(s), since binding specificity is not an absolute, but a relative property. For example, a standard ELISA assay or standard flow cytometry assay can be carried out. The scoring may be carried out by standard color development (e.g. secondary antibody with horseradish peroxide and tetramethyl benzidine with hydrogen peroxide) or by binding of a secondary antibody labeled with PE or another dye or marker. The reaction in certain wells is scored by the optical density (OD), for example, at 450 nm or by mean fluorescence intensity (MFI) in flow cytometry. Typical background (=negative reaction) may be 0.1 OD; typical positive reaction may be 1 OD. Background and positive reaction MFI are highly dependent on instrument settings. The difference positive/negative can be more than 10-fold. Typically, determination of binding specificity is performed by using not a single reference antigen, but a set of about three to five unrelated antigens, such as milk powder, BSA, transferrin or the like. For flow cytometry various antigen-negative cells can be used. An antibody that specifically binds to an antigen may however have cross-reactivity to the respective orthologous antigen from other species (e.g., species homologs). In certain embodiments such cross-reactivity to an orthologous antigen is even preferred.

As used herein, an antibody has "cross-reactivity" or is "cross-reactive" if it binds to the orthologous antigen from other species. For example, an antibody is cross-reactive if it binds to human CCR2 and to marmoset CCR2.

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

The term "epitope" includes any proteinaceous region which is specifically recognized by an antibody or antibody fragment thereof or otherwise interacts with a molecule. Generally, epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

The term "domain" or "protein domain" refers to a region of a protein's polypeptide chain that forms a functional unit and/or independently forms a three-dimensional structure. For example the ECL2 of CCR2 is a protein domain.

"Compositions" of the present disclosure may be used for therapeutic or prophylactic applications. The present disclosure, therefore, includes a pharmaceutical composition containing an antibody or antibody fragment as disclosed herein and a pharmaceutically acceptable carrier or excipient therefore. In a related aspect, the present disclosure provides a method for treating inflammatory diseases, autoimmune diseases, hematologic malignancies and potentially other diseases. Such method contains the steps of administering to a subject in need thereof an effective amount of the pharmaceutical composition that contains an antibody or antibody fragment as described herein.

The present disclosure provides therapeutic methods comprising the administration of a therapeutically effective amount of an antibody or antibody fragment as disclosed herein to a subject in need of such treatment. A "therapeutically effective amount" or "effective amount", as used herein, refers to the amount of a CCR2 antibody necessary to elicit the desired biological response. In accordance with the subject disclosure, the therapeutic effective amount is the amount of a CCR2 antibody necessary to treat and/or prevent a disease.

"Administered" or "administration" includes but is not limited to delivery of a drug by an injectable form, such as, for example, an intravenous, intramuscular, intradermal or subcutaneous route or mucosal route, for example, as a nasal spray or aerosol for inhalation or as an ingestible solution, capsule or tablet. Preferably, the administration is by an injectable form.

As used herein, "treatment", "treat" or "treating" and the like refers to clinical intervention in an attempt to alter the natural course of a disease in the subject being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or antibody fragments according to the preset disclosure are used to delay development of a disease or to slow the progression of a disease.

"Preventing" or "prevention" refers to a reduction in risk of acquiring or developing a disease (i.e. causing at least one of the clinical symptoms of the disease not to develop in a subject that may be exposed to a disease-causing agent, or predisposed to the disease in advance of disease onset). "Prevention" also refers to methods which aim to prevent the onset of a disease or its symptoms or which delay the onset of a disease or its symptoms.

"Subject" or "species" or as used in this context refers to any mammal, including rodents, such as mouse or rat, and primates, such as cynomolgus monkey (*Macaca fascicularis*), Marmoset monkey (*Callithrix jacchus*), rhesus monkey (*Macaca mulatta*) or humans (*Homo sapiens*). Preferably, the subject is a primate, most preferably a human.

The term "effector function" refers to those biological activities attributable to the Fc region of an antibody, which vary with the antibody isotype. Non-limiting examples of antibody effector functions include C1 q binding and complement dependent cytotoxicity (CDC); Fc receptor binding and antibody-dependent cell-mediated cytotoxicity (ADCC) and/or antibody-dependent cellular phagocytosis (ADCP); down regulation of cell surface receptors (e.g. B cell receptor); and direct cell activation or direct cell inhibition.

"Antibody-dependent cell-mediated cytotoxicity" or "ADCC" refers to a form of cytotoxicity in which antibodies bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes/macrophages express FcγRI, FcγRII, and FcγRIII.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) of the present disclosure, which are bound to their cognate antigen.

"Antibody-dependent cellular phagocytosis" or "ADCP" refers to a mechanism of elimination of antibody-coated target cells by internalization by phagocytic cells, such as macrophages or dendritic cells.

Throughout this specification, unless the context requires otherwise, the words "comprise", "have" and "include" and their respective variations such as "comprises", "comprising", "has", "having", "includes" and "including" will be understood to imply the inclusion of a stated element or integer or group of elements or integers but not the exclusion of any other element or integer or group of elements or integers.

The terms "engineered" or "modified" as used herein includes manipulation of nucleic acids or polypeptides by synthetic means (e.g. by recombinant techniques, in vitro peptide synthesis, by enzymatic or chemical coupling of peptides or some combination of these techniques). Preferably, the antibodies or antibody fragments according to the present disclosure are engineered or modified to improve one or more properties, such as antigen binding, stability, half-life, effector function, immunogenicity, safety and the like.

"Variant" as used herein refers to a polypeptide that differs from a reference polypeptide by one or more modifications for example amino acid substitutions, insertions or deletions. Variant polypeptides typically retain most of the properties of the reference polypeptide, e.g. binding to the target antigen, but introduce a novel, additional feature or property, e.g. the variant polypeptide has a higher affinity to the target antigen compared to the reference polypeptide or the variant polypeptide is a humanized version of the reference polypeptide.

The term "amino acid mutation" as used herein is meant to encompass amino acid substitutions, deletions, insertions, and modifications. Any combination of substitution, deletion, insertion, and modification can be made as long as the final construct possesses the desired characteristics, e.g., reduced binding to an Fc receptor. Amino acid sequence deletions and insertions include N- and/or C-terminal deletions and insertions of amino acid residues. Particular amino acid mutations are amino acid substitutions. Amino acid substitutions include replacement by non-naturally occurring amino acids or by naturally occurring amino acid derivatives of the twenty standard amino acids. Amino acid mutations can be generated using genetic or chemical methods well known in the art. Genetic methods may include site-directed mutagenesis, PCR, gene synthesis and the like. It is contemplated that methods of altering the side chain group of an amino acid residue by methods other than genetic engineering, such as chemical modification, may also be useful. Various designations may be used herein to indicate the same amino acid mutation. For example, a substitution from glyince at position 327 of the Fc region to alanine can be indicated as 237A, G337, G337A, or Gly329A1a.

The term "EC50" as used herein, refers to the concentration of an antibody or antibody fragment, which induces a response in an assay half way between the baseline and maximum.

It therefore represents the antibody or ligand concentration at which 50% of the maximal effect is observed.

The terms "inhibition" or "inhibit" or "reduction" or "reduce" or "neutralization" or "neutralize" refer to a decrease or cessation of any phenotypic characteristic (such as binding or a biological activity or function) or to the decrease or cessation in the incidence, degree, or likelihood of that characteristic. "Inhibition", "reduction" or "neutralization" needs not to be complete as long as it is detectable using an appropriate assay. In some embodiments, by "reduce" or "inhibit" or "neutralize" is meant the ability to cause a decrease of 20% or greater. In another embodiment, by "reduce" or "inhibit" or "neutralize" is meant the ability to cause a decrease of 50% or greater. In yet another embodiment, by "reduce" or "inhibit" or "neutralize" is meant the ability to cause an overall decrease of 75%, 85%, 90%, 95%, or greater.

The term "antagonistic" antibody as used herein refers to an antibody or antibody fragment that interacts with an antigen and partially or fully inhibits or neutralizes a biological activity or function or any other phenotypic characteristic of a target antigen.

A "wild-type" protein is a version or variant of the protein as it is found in nature. An amino acid sequence of a wildtype protein, e.g., a Fc region of an human lgG1 antibody, is the amino acid sequence of the protein as it occurs in nature. Due to allotypic differences, there can be more than one amino acid sequence for a wildtype protein. For example, there are several allotypes of naturally occurring human IGg1 heavy chain constant regions (see, e.g., Jeffries et al. (2009) mAbs 1:1).

The "Fc region" is used to define the C-terminal region of an immunoglobulin heavy chain. The Fc region of an immunoglobulin generally comprises two constant domains, a CH2 domain and a CH3 domain. Although the boundaries of the Fc region of an IgG heavy chain might vary slightly, the human IgG heavy chain Fc region is usually defined to extend from Cys226, or from Pro230, to the C-terminus of the heavy chain. However, the C-terminal lysine (Lys447) of the Fc region may or may not be present. Unless otherwise specified herein, numbering of amino acid residues in the Fc region is according to the EU numbering system, also called the EU index, as described in Kabat et al., Sequences of Proteins of Immunological Interest, 5$^{th}$ Ed. Public Health Service, National Institutes of Health, Bethesda, MD, 1991.

Polypeptides

In an embodiment, the present disclosure relates to an isolated antibody or antibody fragment specific for human CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment specific for human CCR2, wherein said antibody or antibody fragment contains the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, as defined by Kabat.

In an embodiment, the present disclosure relates to an isolated antibody or antibody fragment specific for human CCR2, wherein said antibody or antibody fragment contains the HCDR1 region of SEQ ID NO: 16, the HCDR2 region of SEQ ID NO: 17, the HCDR3 region of SEQ ID NO: 18, the LCDR1 region of SEQ ID NO: 19, the LCDR2 region of SEQ ID NO: 20 and the LCDR3 region of SEQ ID NO: 21, as defined by IMGT.

In an embodiment, the present disclosure relates to an isolated antibody or antibody fragment specific for human CCR2 comprising 6 CDRs defined by Kabat of any one of the antibodies disclosed in Table 3.

In an embodiment, the present disclosure relates to an isolated antibody or antibody fragment specific for human CCR2 comprising 6 CDRs defined by IMGT of any one of the antibodies disclosed in Table 3.

In an embodiment, the present disclosure relates to an isolated antibody or antibody fragment specific for human CCR2 comprising 6 CDRs defined by Chothia of any one of the antibodies disclosed in Table 3.

In an embodiment of the present disclosure, the isolated antibody or antibody fragment is a monoclonal antibody or antibody fragment.

In an embodiment of the present disclosure, the isolated antibody or antibody fragment is a human, humanized or chimeric antibody or antibody fragment. In another preferred embodiment of the present disclosure, the isolated antibody or antibody fragment is a humanized antibody or antibody fragment.

In an embodiment of the present disclosure, the isolated antibody or antibody fragment is recombinant antibody or antibody fragment.

In an embodiment of the present disclosure, the isolated antibody or antibody fragment is of the IgG isotype.

In an embodiment of the present disclosure, the isolated antibody or antibody fragment is of the lgG1 class.

In another embodiment of the present disclosure, the isolated antibody or antibody fragment binds to the ECL-2 domain (SEQ ID NO: 2) of human CCR2.

In another embodiment of the present disclosure, the isolated antibody or antibody fragment binds to a polypeptide comprising the ECL-2 domain (SEQ ID NO: 2) of human CCR2.

In another embodiment of the present disclosure, the isolated antibody or antibody fragment specific for human CCR2 is cross-reactive with marmoset CCR2.

In another embodiment of the present disclosure, the isolated antibody or antibody fragment specific for human CCR2 is cross-reactive with marmoset CCR2, but not rhesus CCR2.

In another embodiment of the present disclosure, the isolated antibody or antibody fragment specific for human CCR2 does not bind to rhesus CCR2.

In another embodiment of the present disclosure, the isolated antibody or antibody fragment specific for human CCR2 does not bind to mouse CCR2.

In another embodiment of the present disclosure, the isolated antibody or antibody fragment specific for human CCR2 does not bind to human CCR5 (SEQ ID NO: 6).

In another embodiment of the present disclosure, the isolated antibody or antibody fragment specific for human CCR2 blocks MCP-1 induced downregulation of CCR2 on human leukocytes.

In another embodiment of the present disclosure, the isolated antibody or antibody fragment specific for human CCR2 binds at least 2-fold, at least 3-fold, at least 5-fold or at-least 10-fold better to human CCR2 than DOC2. Preferably, the isolated antibody or antibody fragment specific for human CCR2 binds at-least 10-fold better to human CCR2 than antibody DOC2.

In another embodiment of the present disclosure, the isolated antibody or antibody fragment specific for human CCR2 binds at least 2-fold, at least 3-fold, at least 5-fold or at-least 10-fold better to human CCR2 than an antibody comprising a variable heavy chain of SEQ ID No. 28 and a variable heavy chain of SEQ ID No. 29. Preferably, the isolated antibody or antibody fragment specific for human CCR2 binds at-least 10-fold better to human CCR2 than an antibody comprising a variable heavy chain of SEQ ID No. 28 and a variable heavy chain of SEQ ID No. 29.

The present disclosure also relates to antibodies and antibody fragments specific for human CCR2 which have an at least 10-fold higher affinity to human CCR2 than an antibody comprising a variable heavy chain of SEQ ID No. 28 and a variable heavy chain of SEQ ID No. 29.

The present disclosure also relates to antibodies and antibody fragments wherein said antibody or antibody fragment has a higher affinity to human CCR2 expressed on human monocytes than an antibody comprising a variable heavy chain of SEQ ID No. 28 and a variable heavy chain of SEQ ID No. 29. Preferably said antibody or antibody fragment has an at least 2-fold, an at least 3-fold, an at least 5-fold or an at least 10-fold higher affinity to human CCR2 expressed on human monocytes than an antibody comprising a variable heavy chain of SEQ ID No. 28 and a variable heavy chain of SEQ ID No. 29.

The present disclosure also relates to antibodies and antibody fragments wherein said antibody or antibody fragment has a higher affinity to human CCR2 expressed on human monocytes than an antibody comprising a variable heavy chain of SEQ ID No. 28 and a variable heavy chain of SEQ ID No. 29 at an antibody concentration between 0.1-1.0 µg/ml. Preferably said antibody or antibody fragment has an at least 2-fold, an at least 3-fold, an at least 5-fold or an at least 10-fold higher affinity to human CCR2 expressed on human monocytes than an antibody comprising a variable heavy chain of SEQ ID No. 28 and a variable heavy chain of SEQ ID No. 29.

In another embodiment of the present disclosure, the isolated antibody or antibody fragment specific for human CCR2 has an at least 2-fold, an at least 3-fold, an at least 5-fold or an at-least 10-fold higher affinity to human CCR2 than DOC2. Preferably, the isolated antibody or antibody fragment specific for human CCR2 has an at-least 10-fold higher affinity to human CCR2 than antibody DOC2.

In another embodiment of the present disclosure, the isolated antibody or antibody fragment specific for human CCR2 has an at least 2-fold, an at least 3-fold, an at least 5-fold or an at-least 10-fold higher affinity to human CCR2 than an antibody comprising a variable heavy chain of SEQ ID No. 28 and a variable heavy chain of SEQ ID No. 29. Preferably, the isolated antibody or antibody fragment specific for human CCR2 has an at-least 10-fold higher affinity to human CCR2 than an antibody comprising a variable heavy chain of SEQ ID No. 28 and a variable heavy chain of SEQ ID No. 29.

In another embodiment of the present disclosure, the isolated antibody or antibody fragment specific for human CCR2 binds at least 2-fold, at least 3-fold, at least 5-fold, at-least 10-fold, a at least 20-fold or at least 30-fold better to human CCR2 than antibody 1D9. Preferably, the isolated antibody or antibody fragment specific for human CCR2 binds at least 30-fold better to human CCR2 than antibody 1D9.

In another embodiment of the present disclosure, the isolated antibody or antibody fragment specific for human CCR2 binds at least 2-fold, at least 3-fold, at least 5-fold, at-least 10-fold, at least 20-fold, at least 30-fold, at least 50-fold or at least 100-fold better to human CCR2 than antibody clone 48607. Preferably, the isolated antibody or antibody fragment specific for human CCR2 binds at-least 30-fold better to human CCR2 than antibody clone 48607. Preferably, the isolated antibody or antibody fragment specific for human CCR2 binds at least 100-fold better to human CCR2 than antibody clone 48607.

The antibody referred to herein as "Clone 48607" or "antibody clone 40867" refers to the CD-designating antibody clone 48607. This antibody clone is commercially available (R&D Systems; Catalogue #: MAB150).

In an embodiment, the present disclosure relates to an isolated antibody or antibody fragment specific for human CCR2 comprising the variable heavy chain (VH) of SEQ ID NO: 22 and the variable light chain (VL) of SEQ ID NO: 23.

In an embodiment, the present disclosure relates to an isolated antibody or antibody fragment specific for human CCR2 with the variable heavy chain (VH) of SEQ ID NO: 22 and the variable light chain (VL) of SEQ ID NO: 23.

In an embodiment, the present disclosure relates to an isolated antibody or antibody fragment specific for human CCR2 comprising the variable heavy chain (VH) and the variable light chain (VL) of any one of the antibodies disclosed in Table 3.

In an embodiment, the present disclosure relates to an isolated antibody or antibody fragment specific for human CCR2 comprising a variable heavy chain (VH) with at least at 80% identity to the VH of SEQ ID NO: 22 and a variable light chain (VL) with at least at 80% identity to the variable light chain (VL) of SEQ ID NO: 23.

In an embodiment, the present disclosure relates to an isolated antibody or antibody fragment specific for human CCR2 comprising a variable heavy chain (VH) with at least at 85% identity to the VH of SEQ ID NO: 22 and a variable light chain (VL) with at least at 85% identity to the variable light chain (VL) of SEQ ID NO: 23.

In an embodiment, the present disclosure relates to an isolated antibody or antibody fragment specific for human CCR2 comprising a variable heavy chain (VH) with at least at 90% identity to the VH of SEQ ID NO: 22 and a variable light chain (VL) with at least at 90% identity to the variable light chain (VL) of SEQ ID NO: 23.

In an embodiment, the present disclosure relates to an isolated antibody or antibody fragment specific for human CCR2 comprising a variable heavy chain (VH) with at least at 95% identity to the VH of SEQ ID NO: 22 and a variable light chain (VL) with at least at 95% identity to the variable light chain (VL) of SEQ ID NO: 23.

In an embodiment, the present disclosure relates to an isolated antibody or antibody fragment specific for human CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14, the LCDR3 region of SEQ ID NO: 15, and a variable heavy chain (VH) with at least at 80% identity to the VH of SEQ ID NO: 22 and a variable light chain (VL) with at least at 80% identity to the variable light chain (VL) of SEQ ID NO: 23.

In an embodiment, the present disclosure relates to an isolated antibody or antibody fragment specific for human CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14, the LCDR3 region of SEQ ID NO: 15, and a variable heavy chain (VH) with at least at 85% identity to the VH of SEQ ID NO: 22 and a variable light chain (VL) with at least at 85% identity to the variable light chain (VL) of SEQ ID NO: 23.

In an embodiment, the present disclosure relates to an isolated antibody or antibody fragment specific for human CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14, the LCDR3 region of SEQ ID NO: 15, and a variable heavy chain (VH) with at least at 90% identity to the VH of SEQ ID NO: 22 and a variable light chain (VL) with at least at 90% identity to the variable light chain (VL) of SEQ ID NO: 23.

In an embodiment, the present disclosure relates to an isolated antibody or antibody fragment specific for human CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14, the LCDR3 region of SEQ ID NO: 15, and a variable heavy chain (VH) with at least at 95% identity to the VH of SEQ ID NO: 22 and a variable light chain (VL) with at least at 95% identity to the variable light chain (VL) of SEQ ID NO: 23.

Nucleic Acids

In an embodiment, the present disclosure relates to a nucleic acid composition comprising a nucleic acid sequence or a plurality of nucleic acid sequences encoding an isolated antibody or antibody fragment specific for human CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to a nucleic acid composition comprising a nucleic acid sequence or a plurality of nucleic acid sequences encoding an isolated antibody or antibody fragment specific for human CCR2, wherein said antibody or antibody fragment contains the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, as defined by Kabat.

In an embodiment, the present disclosure relates to a nucleic acid composition comprising a nucleic acid sequence or a plurality of nucleic acid sequences encoding an isolated antibody or antibody fragment specific for human CCR2, wherein said antibody or antibody fragment contains the HCDR1 region of SEQ ID NO: 16, the HCDR2 region of SEQ ID NO: 17, the HCDR3 region of SEQ ID NO: 18, the LCDR1 region of SEQ ID NO: 19, the LCDR2 region of SEQ ID NO: 20 and the LCDR3 region of SEQ ID NO: 21, as defined by IMGT.

In an embodiment, the present disclosure relates to a nucleic acid composition comprising a nucleic acid sequence or a plurality of nucleic acid sequences encoding an isolated antibody or antibody fragment specific for human CCR2, wherein said antibody or antibody fragment comprises a variable heavy chain (VH) of SEQ ID NO: 22 and a variable light chain (VL) of SEQ ID NO: 23.

In an embodiment, the present disclosure relates to a nucleic acid composition comprising a nucleic acid sequence or a plurality of nucleic acid sequences encoding an isolated antibody or antibody fragment specific for human CCR2, wherein said antibody or antibody fragment contains a variable heavy chain (VH) of SEQ ID NO: 22 and a variable light chain (VL) of SEQ ID NO: 23.

In an embodiment, the present disclosure relates to a nucleic acid composition comprising a nucleic acid sequence or a plurality of nucleic acid sequences encoding an isolated antibody or antibody fragment specific for human CCR2 comprising 6 CDRs defined by Kabat of any one of the antibodies disclosed in Table 3.

In an embodiment, the present disclosure relates to a nucleic acid composition comprising a nucleic acid sequence or a plurality of nucleic acid sequences encoding an isolated antibody or antibody fragment specific for human CCR2 comprising 6 CDRs defined by IMGT of any one of the antibodies disclosed in Table 3.

In an embodiment, the present disclosure relates to a nucleic acid composition comprising a nucleic acid sequence or a plurality of nucleic acid sequences encoding an isolated antibody or antibody fragment specific for human CCR2 comprising 6 CDRs defined by Chothia of any one of the antibodies disclosed in Table 3.

In an embodiment, said nucleic acid composition and/or said.nucleic acid sequence and/or plurality of nucleic acid sequences are isolated.

Vectors

In an embodiment, the present disclosure provides a vector composition comprising a vector or a plurality of vectors comprising a nucleic acid composition comprising a nucleic acid sequence or a plurality of nucleic acid sequences encoding an isolated antibody or antibody fragment specific for human CCR2 according to the present disclosure.

In an embodiment, the present disclosure provides a vector composition comprising a vector or a plurality of vectors comprising a nucleic acid composition comprising a nucleic acid sequence or a plurality of nucleic acid sequences encoding any one of the isolated antibodies or antibody fragments specific for human CCR2 disclosed in Table 3.

In an embodiment, said vector composition and/or vector and/or plurality of vectors are isolated.

Host Cells

In an embodiment, the present disclosure provides a host cell comprising a vector composition comprising a vector or a plurality of vectors comprising a nucleic acid composition comprising a nucleic acid sequence or a plurality of nucleic acid sequences encoding an isolated antibody or antibody fragment specific for human CCR2 according to the present disclosure.

In an embodiment, the present disclosure refers to a host cell comprising a vector composition comprising a vector or a plurality of vectors comprising a nucleic acid composition comprising a nucleic acid sequence or a plurality of nucleic acid sequences encoding an isolated antibody or antibody fragment specific for CCR2 disclosed in Table 3.

In an embodiment, the host cell according to the present disclosure is able to express the isolated antibody or antibody fragment specific for human CCR2 encoded by the vector composition or the nucleic acid composition.

In a further embodiment, the host cell is an isolated host cell. In a further embodiment, said host cell is a mammalian cell. In an embodiment, said mammalian cell is a human cell. In another embodiment, said mammalian cell is a CHO cell. In an embodiment, said cell is a HEK cell. In another embodiment, said cell is a PERC.6 cell. In an embodiment, said cell is a HKB1 1 cell.

The skilled man will realize that the nucleic acid sequence or the plurality of nucleic acid sequences encoding the heavy and/or light chain of an antibody or antibody fragment of the present disclosure can be cloned into different vectors or into the same vector.

The vectors can be introduced into the appropriate host cells such as prokaryotic (e.g., bacterial) or eukaryotic (e.g., yeast or mammalian) cells by methods well known in the art (see e.g., "Current Protocol in Molecular Biology", Ausubel et al. (eds.), Greene Publishing Assoc and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the nucleic acid sequence encoding the desired protein is transcribed into RNA in the host cell transformed by a vector containing this expression construction. The coding sequence may or may not contain a signal peptide or leader sequence. Upon expression in host cells, the antibodies or antibody fragments of the present disclosure are obtained. These steps can be achieved in different ways, as will be known by the person skilled in the art. In general, such steps typically include transforming or transfecting a suitable host cell with a nucleic acid composition or vector composition or an infectious particle, which encodes the antibody, or antibody fragments. Further, such steps typically include culturing said host cells under conditions suitable for the proliferation (multiplication, growth) of said host cells and a culturing step under conditions suitable for the production (expression, synthesis) of the encoded antibody or antibody fragment. The culturing of host cells under conditions suitable for proliferation or expression is typically accomplished in the presence of media comprising components suitable for cell growth or induction of expression. In particular, embodiments, the methods for the production of the antibodies or antibody fragments of the present disclosure further comprise the step of isolating and purifying the produced antibody or antibody fragment from the host cells or medium. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art. The antibody or antibody fragment of the present disclosure can then be purified by a number of techniques as known to the person skilled in the art.

In an embodiment, the present disclosure refers to a method of producing an isolated antibody or antibody fragment specific for human CCR2 of any of the antibodies disclosed in Table 3. In an embodiment, a method of producing an isolated antibody or antibody fragment according to the present disclosure is provided, wherein the method comprises culturing a host cell comprising a vector composition comprising a vector or a plurality of vectors comprising a nucleic acid composition comprising a nucleic acid sequence or a plurality of nucleic acid sequences encoding an antibody or antibody fragment according to the present disclosure, under conditions suitable for expression of the antibody or antibody fragment, and isolating the antibody or antibody fragment from the host cell or host cell culture medium. An antibody or antibody fragment isolated as described herein may be purified techniques know in the art, such as high performance liquid chromatography (HPLC), ion exchange chromatography, gel electrophoresis, affinity chromatography, size exclusion chromatography, and the like. The conditions used to purify a particular antibody or antibody fragment will depend, in part, on factors such as net charge, hydrophobicity, hydrophilicity etc., and will be apparent to those having skill in the art. For affinity chromatography purification an antibody, ligand, receptor or antigen can be used to which the antibody or antibody fragment binds. For example, for affinity chromatography purification of antibody or antibody fragment according to the present disclosure, a matrix with protein A or protein G may be used. The purity of an antibody or antibody fragment can be determined by any of a variety of well-known analytical methods including gel electrophoresis, high-pressure liquid chromatography, and the like.

Specificity

In an embodiment, the present disclosure relates to an isolated antibody or antibody fragment specific for human CCR2 disclosed in Table 3.

In an embodiment, the present disclosure relates to an isolated antibody or antibody fragment specific for human CCR2.

In an embodiment, the present disclosure relates to an isolated antibody or antibody fragment specific for a polypeptide encoded by the amino acid sequence of SEQ ID NO: 1.

In an embodiment, the present disclosure relates to an isolated antibody or antibody fragment specific for a polypeptide comprising the amino acid sequence of SEQ ID NO: 1.

In an embodiment, the isolated antibody or antibody fragment binds to an extracellular domain of human CCR2.

In an embodiment, the isolated antibody or antibody fragment binds to the extracellular domain 2 (ECL2) of human CCR2.

In an embodiment, the present disclosure relates to an isolated antibody or antibody fragment specific for the ECL-2 domain (SEQ ID NO: 2) of human CCR2.

In an embodiment, the present disclosure relates to an isolated antibody or antibody fragment wherein said antibody or antibody fragment binds to the ECL-2 domain (SEQ ID NO: 2) of human CCR2.

In an embodiment, the present disclosure relates to an isolated antibody or antibody fragment that is specific to marmoset CCR2.

In an embodiment, the present disclosure relates to an isolated antibody or antibody fragment specific for a polypeptide encoded by the amino acid sequence of SEQ ID NO: 2.

In an embodiment, the present disclosure relates to an isolated antibody or antibody fragment specific for a polypeptide comprising the amino acid sequence of SEQ ID NO: 2.

In an embodiment, the present disclosure relates to an isolated antibody or antibody fragment that is cross-reactive to marmoset CCR2.

In an embodiment, the present disclosure relates to an isolated antibody or antibody fragment specific for human CCR2 and marmoset CCR2.

In an embodiment, the present disclosure relates to an isolated antibody or antibody fragment specific for human CCR2 and marmoset CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment specific for human CCR2 and marmoset CCR2, wherein said antibody or antibody fragment contains the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment specific for human CCR2 and does not bind to rhesus CCR2.

In an embodiment, the present disclosure relates to an isolated antibody or antibody fragment specific for human CCR2 and does not bind to rhesus CCR2, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment specific for human CCR2 and does not bind to rhesus CCR2, wherein said antibody or antibody fragment contains the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment specific for human CCR2 which does not bind human CCR5.

In an embodiment, the present disclosure relates to an isolated antibody or antibody fragment specific for a polypeptide encoded by the amino acid sequence of SEQ ID NO: 1, which does not bind to a polypeptide encoded by the amino acid sequence of SEQ ID NO: 6.

In an embodiment, the present disclosure relates to an isolated antibody or antibody fragment which does bind to a polypeptide encoded by the amino acid sequence of SEQ ID NO: 1 and does not bind to a polypeptide encoded by the amino acid sequence of SEQ ID NO: 6.

In an embodiment, the present disclosure relates to an isolated antibody or antibody fragment which binds to the extracellular domain 2 (ECL2) of human CCR2 and does not bind to a polypeptide encoded by the amino acid sequence of SEQ ID NO: 6.

In an embodiment, the present disclosure relates to an isolated antibody or antibody fragment wherein said antibody or antibody fragment binds to the ECL-2 domain (SEQ ID NO: 2) of human CCR2 and does not bind to a polypeptide encoded by the amino acid sequence of SEQ ID NO: 6.

In an embodiment, the present disclosure relates to an isolated antibody or antibody fragment wherein said antibody or antibody fragment binds to the ECL-2 domain (SEQ ID NO: 2) of human CCR2, binds to a polypeptide encoded by the amino acid sequence of SEQ ID NO: 3 and does not bind to a polypeptide encoded by the amino acid sequence of SEQ ID NO: 6.

In an embodiment, the present disclosure relates to an isolated antibody or antibody fragment wherein said antibody or antibody fragment binds to a polypeptide encoded by the amino acid sequence of SEQ ID NO: 1, binds to a polypeptide encoded by the amino acid sequence of SEQ ID NO: 3 and does not bind to a polypeptide encoded by the amino acid sequence of SEQ ID NO: 6.

In an embodiment, the present disclosure relates to an isolated antibody or antibody fragment wherein said antibody or antibody fragment binds to a polypeptide encoded by the amino acid sequence of SEQ ID NO: 1, binds to a polypeptide encoded by the amino acid sequence of SEQ ID NO: 3 and does not bind to a polypeptide encoded by the amino acid sequence of SEQ ID NO: 6, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment wherein said antibody or antibody fragment binds to a polypeptide encoded by the amino acid sequence of SEQ ID NO: 1, binds to a polypeptide encoded by the amino acid sequence of SEQ ID NO: 3 and does not bind to a polypeptide encoded by the amino acid sequence of SEQ ID NO: 6, wherein said antibody or antibody fragment has the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15.

In an embodiment, the present disclosure relates to an isolated antibody or antibody fragment wherein said antibody or antibody fragment binds to a polypeptide encoded by the amino acid sequence of SEQ ID NO: 1, binds to a polypeptide encoded by the amino acid sequence of SEQ ID NO: 3 and does not bind to a polypeptide encoded by the amino acid sequence of SEQ ID NO: 6, wherein said antibody or antibody fragment comprises a variable heavy chain (VH) of SEQ ID NO: 22 and a variable light chain (VL) of SEQ ID NO: 23.

In an embodiment, the present disclosure relates to an isolated antibody or antibody fragment wherein said antibody or antibody fragment binds to a polypeptide encoded by the amino acid sequence of SEQ ID NO: 1, binds to a polypeptide encoded by the amino acid sequence of SEQ ID NO: 3 and does not bind to a polypeptide encoded by the amino acid sequence of SEQ ID NO: 6, wherein said antibody or antibody fragment has a variable heavy chain (VH) of SEQ ID NO: 22 and a variable light chain (VL) of SEQ ID NO: 23.

Effect on Leukocytes

CCR2 and MCP-1 play a key role in the migration of monocytes to sites of inflammation. The antibodies and antibody fragments of the present disclosure play a key role in this process and form the basis for the therapeutic usefulness of the antibodies and antibody fragments of the present disclosure.

In an embodiment, the present disclosure relates to an isolated antibody or antibody fragment blocking the MCP-1 induced downregulation of CCR2 on leukocytes. In an embodiment, the present disclosure relates to an isolated antibody or antibody fragment blocking the MCP-1 induced downregulation of CCR2 on human leukocytes.

In an embodiment, the present disclosure relates to an isolated antibody or antibody fragment blocking the MCP-1 induced downregulation of CCR2 on monocytes. In an embodiment, the present disclosure relates to an isolated antibody or antibody fragment blocking the MCP-1 induced downregulation of CCR2 on human monocytes.

In an embodiment, the present disclosure relates to an isolated antibody or antibody fragment blocking the MCP-1 induced downregulation of CCR2 on basophils and plasmacytoid dendritic cells. In an embodiment, the present disclosure relates to an isolated antibody or antibody fragment blocking the MCP-1 induced downregulation of CCR2 on human basophils and plasmacytoid dendritic cells.

In an embodiment, the present disclosure relates to an isolated antibody or antibody fragment inhibit CCR2-induced chemotaxis in leukocytes. In an embodiment, the present disclosure relates to an isolated antibody or antibody fragment inhibit CCR2-induced chemotaxis in monocytes. In an embodiment, the present disclosure relates to an isolated antibody or antibody fragment inhibit CCR2-induced chemotaxis in basophils and plasmacytoid dendritic cells.

Effector Function

The Fc region of an immunoglobulin generally confers to the favorable pharmacokinetic properties of antibodies, such as prolonged half-life in serum and to the ability to induce effector function via binding to Fc receptors expressed on cells. On the other hand, binding to Fc receptors might also results in an undesirable activation of certain cell surface receptors leading to unwanted cytokine release and severe side effects upon systemic administration.

Accordingly, for certain therapeutic situations, it is desirable to reduce or abolish the normal binding of the wild-type Fc region of an antibody, such as of an wild-type IgG Fc region to one or more or all of Fc receptors and/or binding to a complement component, such as C1 q in order to reduce or abolish the ability of the antibody to induce effector function. For instance, it may be desirable to reduce or abolish the binding of the Fc region of an antibody to one or more or all of the Fcγ receptors, such as: FcγRI, FcγRIIa, FcγRIIb, FcγRIIIa. Effector function can include, but is not limited to, one or more of the following: complement dependent cytotoxicity (CDC), antibody-dependent cell-mediated cytotoxicity (ADCC), antibody-dependent cellular phagocytosis (ADCP), cytokine secretion, immune complex-mediated antigen uptake by antigen-presenting cells, binding to NK cells, binding to macrophages, binding to monocytes, binding to polymorphonuclear cells, direct signaling inducing apoptosis, crosslinking of target-bound antibodies, dendritic cell maturation, or T cell priming.

A reduced or abolished binding of an Fc region to an Fc receptor and/or to C1 q is typically achieved by mutating a wild-type Fc region, such as of an lgG1 Fc region, more particular a human IgG1 Fc region, resulting in a variant or engineered Fc region of said wild-type Fc region, e.g. a variant human lgG1 Fc region. Substitutions that result in reduced binding can be useful. For reducing or abolishing the binding properties of an Fc region to an Fc receptor, non-conservative amino acid substitutions, i.e. replacing one amino acid with another amino acid having different structural and/or chemical properties, are preferred.

Accordingly, in an embodiment, the isolated antibody or antibody fragment specific for human CCR2 according to the present disclosure comprises a variant Fc region having a reduced or abolished binding to an Fc receptor and/or to C1q when compared to the wild-type Fc region. In one such embodiment, the isolated antibody or antibody fragment according to the present disclosure comprises a variant Fc region that reduces or abolishes the ability of the antibody to induce effector function. In a further embodiment, the isolated antibody or antibody fragment according to the present disclosure does not substantially induce effector function.

In certain embodiments, the effector function is one or more selected from the group consisting of CDC, ADCC and ADCP. In an embodiment, the effector function is ADCC. In an embodiment, the effector function is CDC. In an embodiment, the effector function is ADCP. In an embodiment, the isolated antibody or antibody fragment according to the present disclosure does not substantially induce ADCC and/or CDC and/or ADCP. In an embodiment, the isolated antibody or antibody fragment according to the present disclosure does not induce ADCC or ADCP in vitro.

In an embodiment, the variant Fc region of the isolated antibody or antibody fragment according to the present disclosure comprises one or more amino acid substitutions that reduce or abolish the binding of the variant Fc region to one or more Fc receptors and/or to C1 q when compared to the wild-type Fc region. In an embodiment, the variant Fc region of the isolated antibody or antibody fragment according to the present disclosure comprises one or more amino acid substitutions that reduce or abolish the ability of the antibody to induce effector function when compared to the wild-type Fc region. In a particular embodiment, the one or more amino acid substitutions may reduce the binding affinity of the variant Fc region for one or more Fc receptors and/or to C1q by at least 2-fold, at least 5-fold, at least 10-fold, at least 20-fold or even at least 50-fold when compared to the wild-type Fc region. In alternative embodiments, the one or more amino acid substitutions may reduce the ability of the isolated antibody or antibody fragment according to the present disclosure to induce effector function by at least 2-fold, at least 5-fold, at least 10-fold, at least 20-fold or even at least 50-fold when compared to the wild-type Fc region.

In an embodiment, the variant Fc region of the isolated antibody or antibody fragment according to the present disclosure does not substantially bind to one or more Fc receptors and/or C1q. In an embodiment, the variant Fc region of the antibody according to the present disclosure does substantially abolish the ability of said antibody to induce effector function. In an embodiment, the antibody or antibody fragment according to the present disclosure does not substantially induce effector function. In an embodiment, said effect function is ADCC and/or ADCP and/or CDC. In an embodiment, the antibody or antibody fragment according to the present disclosure does not substantially induce effector function meaning that the level of induced effector function is not significantly above the background as measured in the absence of said antibody.

In an embodiment, the Fc receptor is a human Fc receptor. In an embodiment, the Fc receptor is an Fcy receptor. In an embodiment, the Fc receptor is a human FcγRIIIa, FcγRI, FcγRIIa and/or FcγRIIb.

In an embodiment, the isolated antibody or antibody fragment according to the present disclosure comprises a variant human lgG1 Fc region, which comprises one or more amino acid substitutions compared to the wild-type human lgG1 Fc region. In an embodiment, that one or more amino acid substitutions reduce or abolish the binding of the variant Fc region to an Fc receptor and/or to C1 q and/or reduces the ability of said antibody to induce effector function when compared to the wild-type Fc region.

The isolated antibody or antibody fragment according to the present disclosure may or may not be fused to one or more other amino acid residues, polypeptides or moieties. Such a fusion protein may be prepared in any suitable manner, including genetically or chemically approaches. Said linked moieties may contain secretory or leader sequences, sequences that aid detection, expression, separation or purification, or sequences that confer to increased protein stability, for example, during recombinant production. Non-limiting examples of potential moieties include beta-galactosidase, glutathione-S-transferase, luciferase, a T7 polymerase fragment, a secretion signal peptide, an antibody or antibody fragment, a toxin, a reporter enzyme, a moiety being capable of binding a metal ion like a poly-histidine tag, a tag suitable for detection and/or purification, a homo- or hetero-association domain, a moiety which increases solubility of a protein, or a moiety which comprises an enzymatic cleavage site.

Accordingly, the isolated antibody or antibody fragment according to the present disclosure may optionally contain one or more moieties for binding to other targets or target proteins of interest. It should be clear that such further moieties may or may not provide further functionality to the antibody and may or may not modify the properties of the isolated antibody or antibody fragment according to the present disclosure.

Therapeutic Methods

The isolated antibody or antibody fragment according to the present disclosure may be used in therapeutic methods. The antibody or antibody fragment according to the present disclosure may be used for the treatment of inflammatory diseases, autoimmune diseases, hematologic malignancies and potentially other diseases.

In an embodiment, the disease is associated with the undesired presence of CCR2, in human CCR2. In another embodiment, the disease is associated with the undesired presence of CCR2 positive cells, in particular human CCR2 positive cells. Human CCR2 positive cells include CD16-negative monocytes, basophils and plasmacytoid dendritic cells. Also about 20% of CD4+ and CD8+ T cells express CCR2.

In an embodiment, the disease to be treated is an autoimmune or inflammatory disease. Non-limiting examples an autoimmune or inflammatory disease include rheumatoid arthritis (RA), psoriasis, psoriatic arthritis, systemic lupus erythematosus (SLE), lupus nephritis, type I diabetes, Grave's disease, Inflammatory bowel disease (IBD), Crohn's disease (CD), ulcerative colitis (UC), irritable bowel syndrome, multiple sclerosis (MS), Guillain-Barre's Syndrome, autoinflammatory diseases like Familial Mediterranean Fever (FMF), Cryopyrin-associated periodic syndromes (CAPS), Deficiency of IL-1-Receptor Antagonist (DIRA), Hyper IgD Syndrome (HIDS), autoimmune myocarditis, Kawasaki disease, coronary artery disease, chronic obstructive pulmonary disease (COPD), interstitial lung disease, autoimmune thyroiditis, scleroderma, systemic sclerosis, osteoarthritis, atoptic dermatitis, vitiligo, graft vs. host disease, Sjogren's syndrome, autoimmune nephritis, Goodpasture's syndrome, chronic inflammatory demyelinating polyneuropathy, ANCA-associated vasculitis, uveitis, scleroderma, bullous pemphigoid, Alzheimer's Disease, amyotrophic lateral sclerosis, Huntington's Chorea, cystic fibrosis, gout, age-related macular degeneration, allergy, asthma, antiphospholipid syndrome (APS), atherosclerosis, C3 glomerulopathy and IgA nephropathy, ischemia/reperfusion injury, peritonitis, sepsis and other autoimmune diseases that are a result of either acute or chronic inflammation.

In an embodiment, the disease to be treated is a proliferative disease. In a particular embodiment, the disease is cancer. Non-limiting examples of cancers include hematologic malignancies like chronic myelomonocytic leukemia (CMML), acute myeloid leukemia (AML), myelodysplastic syndrome, mastocytosis and non-hematologic malignancies like bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, sarcoma, skin cancer, squamous cell carcinoma, bone cancer, melanoma, renal cell carcinoma, and kidney cancer.

In an embodiment, the present disclosure provides a method for the treatment of a disease.

In an embodiment, the present disclosure provides a method for the treatment of a disease comprising administering to a patient an antibody or antibody fragment of the present disclosure.

In an embodiment, the present disclosure provides a method for the treatment of a disease comprising administering to a subject in need there of an antibody or antibody fragment of the present disclosure.

In an embodiment, the present disclosure provides a method for the prevention of a disease.

In an embodiment, the present disclosure provides a method for the prevention of a disease comprising administering to a subject an antibody or antibody fragment of the present disclosure.

In an embodiment, the present disclosure provides an isolated antibody or antibody fragment according to the present disclosure for the treatment of a disease. In an embodiment, the present disclosure provides an isolated antibody or antibody fragment according to the present disclosure for use in the treatment of a disease. In an embodiment, the present disclosure provides an isolated antibody or antibody fragment according to the present disclosure for use in the treatment of a disease in a subject in need thereof.

In an embodiment, the present disclosure provides the use of an isolated antibody or antibody fragment according to the present disclosure for the manufacture of a medicament. In an embodiment, the present disclosure provides an isolated antibody or antibody fragment according to the present disclosure for use as a medicament. In an embodiment, the present disclosure provides an isolated antibody or antibody fragment according to the present disclosure for use in medicine. In an embodiment, the present disclosure provides an isolated antibody or antibody fragment according to the present disclosure for use as a medicament for the treatment of a subject in need thereof.

In an embodiment, the present disclosure provides an isolated antibody or antibody fragment specific for human CCR2 according to the present disclosure for use in a method of treating a subject having a disease comprising administering to the subject a therapeutically effective amount of an antibody or antibody fragment according to the present disclosure.

In an embodiment, the method further comprises administering to the subject a therapeutically effective amount of at least one additional therapeutic agent. The subject in need of treatment is typically a mammal, more specifically a human. For use in therapeutic methods, an isolated antibody or antibody fragment according to the present disclosure would be formulated, dosed, and administered in a way consistent with good medical practice.

Pharmaceutical Compositions

In an embodiment, the present disclosure provides a pharmaceutical composition comprising an isolated antibody or antibody fragment according to the present disclosure and a pharmaceutically acceptable carrier or excipient.

The pharmaceutical compositions may further comprise at least one other pharmaceutically active compound. The pharmaceutical composition according to the present disclosure can be used in the diagnosis, prevention and/or treatment of diseases associated with the undesired presence of CCR2, in particular human CCR2. The pharmaceutical composition according to the present disclosure can be used in the diagnosis, prevention and/or treatment of diseases associated with the undesired presence of CCR2 positive cells, in particular CCR2 positive human cells. In particular, the present disclosure provides a pharmaceutical compositions comprising an antibody or antibody fragment according to the present disclosure that is suitable for prophylactic, therapeutic and/or diagnostic use in a mammal, more particular in a human.

In general, an antibody or antibody fragment according to the present disclosure may be formulated as a pharmaceutical composition comprising at least one antibody or antibody fragment according to the present disclosure and at least one pharmaceutically acceptable carrier or excipient, and optionally one or more further pharmaceutically active compounds. Such a formulation may be suitable for oral, parenteral, topical administration or for administration by inhalation. Accordingly, a pharmaceutical composition comprising at least one antibody or antibody fragment according to the present disclosure may be administered parenterally, such as intravenously, or intramuscularly, or subcutaneously. Alternatively, an antibody of the invention may be administered via a non-parenteral route, such as per-orally or topically. In a preferred embodiment, a pharmaceutical composition comprising an antibody or antibody fragment according to the present disclosure is administered intravenously or subcutaneously.

In particular, an antibody or antibody fragment according to the present disclosure may be used in combination with one or more pharmaceutically active compounds that are or can be used for the prevention and/or treatment of the diseases in which a target antigen of interest is involved, as a result of which a synergistic effect may or may not be obtained. Examples of such compounds, as well as routes, methods and pharmaceutical formulations or compositions for administering them will be clear to the clinician.

In an embodiment, the present disclosure provides a pharmaceutical composition comprising an antibody or antibody fragment according to the present disclosure for use in the prevention and/or treatment of a disease associated with the undesired presence of CCR2, in particular human CCR2. In an embodiment, the present disclosure provides a pharmaceutical composition comprising an antibody or antibody fragment according to the present disclosure for use in the prevention and/or treatment of a disease associated with the undesired presence of CCR2 positive cells, in particular CCR2 positive human cells. In an embodiment, the present disclosure provides a pharmaceutical composition comprising an antibody or antibody fragment according to the present disclosure for the use as a medicament. In an embodiment, the present disclosure provides a pharmaceutical composition comprising an antibody or antibody fragment according to the present disclosure for use in the prevention and/or treatment of an autoimmune disease and/or inflammatory disease and/or cancer.

In an embodiment, the present disclosure provides a method for the treatment of an autoimmune disease and/or inflammatory disease and/or cancer in a subject in need thereof using a pharmaceutical composition comprising an antibody or antibody fragment according to the present disclosure.

Further provided is a method of producing an antibody or antibody fragment according to the present disclosure in a form suitable for administration in vivo, the method comprising (a) obtaining an antibody or antibody fragment by a method according to the present disclosure, and (b) formulating said antibody or antibody fragment with at least one pharmaceutically acceptable carrier or excipient, whereby a preparation of antibody or antibody fragment is formulated for administration in vivo. Pharmaceutical compositions according to the present disclosure comprise a therapeutically effective amount of one or more antibodies or antibody fragments according to the present disclosure dissolved in a pharmaceutically acceptable carrier or excipient.

Diagnostic Use

In an embodiment, the present disclosure provides the use of an isolated antibody or antibody fragment specific for human CCR2 according to the present disclosure for the diagnosis of a disease. In an embodiment, the present disclosure provides the use of an antibody or antibody fragment according to the present disclosure for the detection of CCR2, in particular human CCR2 and/or marmoset CCR2. In an embodiment, the present disclosure provides a method for detecting CCR2 in a subject or a sample, comprising the step of contacting said subject or sample with an isolated antibody or antibody fragment specific for human CCR2 of the present disclosure. In an embodiment, the present disclosure provides a method for diagnosing a disease in a subject, comprising the step of contacting said subject or sample with an isolated antibody or antibody fragment according to the present disclosure. The antibodies may also be used to determine CCR2 expression levels in cells from patients. The CCR2 expressions levels may serve as therapeutic biomarkers, for example for patient stratification.

EXAMPLES

Example 1: Generation of Anti-CCR2 Antibodies Using Hybridoma Technology

Anti-CCR2 antibodies were generated using classical hybridoma technology. In brief, BALB/c mice were immunized six times at 4-week intervals with 10 million CHO cells stably transfected with human CCR2b. Splenocytes were fused to X63Ag8 myeloma cells and hybridomas were screened for specific binding to CCR2-transfected CHO cells and absence of binding to CCR5-transfected CHO cells. Hybridomas were cloned and recloned by limited dilution technology.

Several anti-CCR2 antibodies were identified and characterized, including antibodies Y4T3, Y2T63 and Y1T2.

Example 2: Specificity for Human CCR2 and Absence of Cross-Reactivity with CCR5

Hybridoma antibodies were tested for binding to human CCR2 expressed in transfected CHO cells. As a control, CHO cells were also transfected with human CCR5. As another control, binding of the anti-CCR5 antibody MC-1 (Mol Biol Cell. 2002 February; 13(2): 723-737, produced in house) to the transfected CHO cells was also tested. Antibodies were tested at concentration of 10 µg/ml and 1 µg/ml and incubated with the cells for 45 min on ice. After 3 washing steps with cold PBS, the bound antibodies were detected with a PE-labeled polyclonal rabbit anti-mouse immunoglobulins antibody (R0439 from Agilent Dako, diluted 1:200 in PBS) for 30 min on ice. After two washing steps with PBS, cells were analyzed by flow cytometry. Mean fluorescence intensity for PE was determined and is depicted.

Results for exemplary antibody Y4T3 are shown in FIG. 1. Anti-CCR2 antibody Y4T3 was specific for human CCR2, but did not show any binding to human CCR5. Anti-CCR5 antibody MC-1 was specific for human CCR5, but did not show any binding to human CCR2.

Example 3: Binding to Human Monocytes

In order to exert their functional effect, the antibodies of the present invention need to bind to CCR2 expressed on human monocytes. Binding to CD16-positive and CD16-negative monocytes was measured. 60 µl of lithium-heparin anticoagulated human whole blood was incubated for 45 min on ice with the indicated antibodies in the indicated concentrations in PBS. After three washing steps with cold PBS the bound antibodies were detected with a PE-labeled polyclonal rabbit anti-mouse immunoglobulins antibody (R0439 from Agilent Dako, diluted 1:200 in PBS) for 30 min on ice. After three washing steps with PBS 10% mouse serum was added and incubated for 10 min on ice. Without further washing directly labelled antibodies against CD3, CD8, CD4, CD123, CD304, CD116 and CD16 were added for 30 min on ice. After 2 washing steps with 0.9% NaCl red blood cells were lysed with Lysing Solution (BDBioscience) for 10 min in the dark. Cells were washed once with PBS and analyzed by flow cytometry to identify CD16-positive and CD16-negative monocytes. Mean fluorescence intensity for PE was determined for these cell populations and is depicted. CCR2 is only expressed in CD16-negative, but not in CD-16 positive monocytes. Two additional anti-CCR2 antibodies were also tested: 1D9, the parental antibody of MLN1202 which was formerly in development by Millennium (BDBioscience) and Clone 48607, a commercially available anti-CCR2 antibody (R&D Systems; Catalogue #: MAB150).

Figure 2:
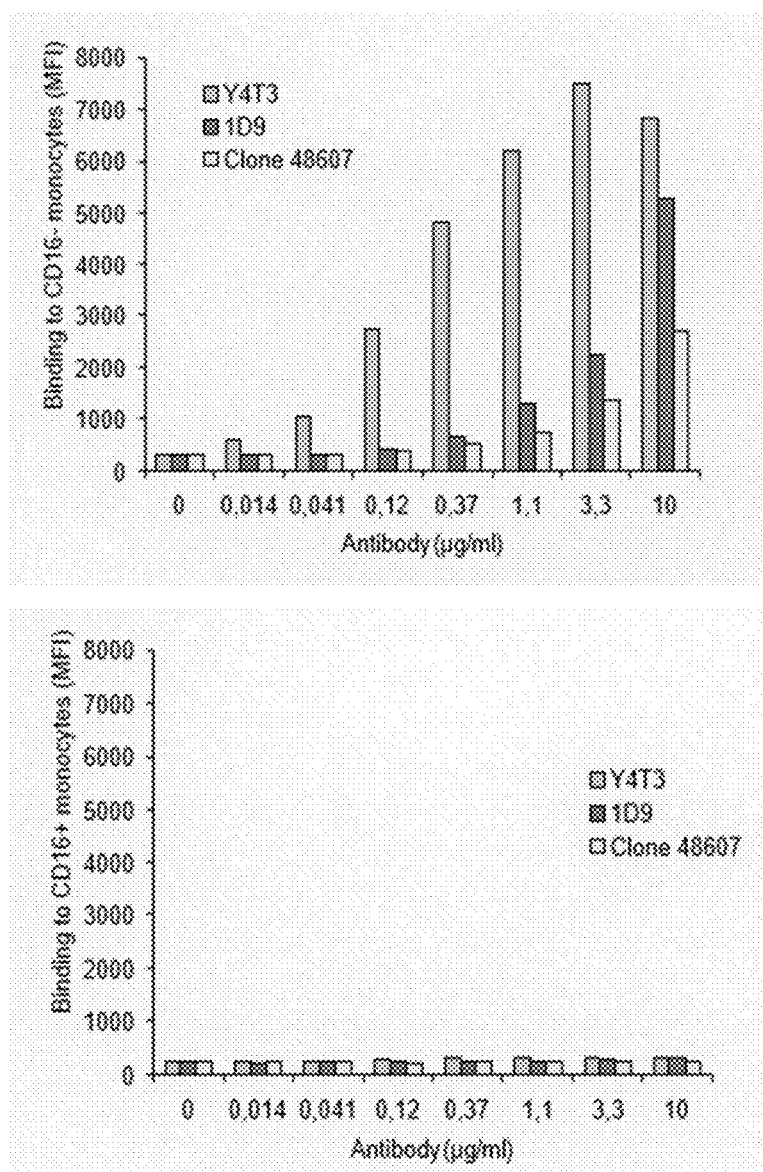
FIG. 2 shows that the antibodies of the present invention bind to CD16-negative monocytes (top panel), but do not bind to CD16-positive monocytes (bottom panel).

Results are shown in FIG. 2. Exemplary antibody Y4T3 was reactive with CD16-negative monocytes, but did not bind to CD16-positive monocytes. Also the control antibodies, 1D9 and Clone 48607, showed binding to CD16-negative monocytes, but not to CD16-positive monocytes. Binding of Y4T3 was however clearly stronger than binding of 1D9 and Clone 48607.

Example 4: Binding to Marmoset Monocytes

Marmoset monkeys are an established animal model. Binding to marmoset CCR2 is therefore highly desirable.

Binding to CD16-positive and CD16-negative marmoset monocytes was measured. DOC-3, an anti-CCR2 antibody with known reactivity to marmoset CCR2 (WO2007/115713), was used as a control. Marmoset splenocytes were incubated for 30 min on ice with the indicated antibodies in the indicated concentrations in PBS. After three washing steps with cold PBS the bound antibodies were detected with a PE-labeled polyclonal rabbit anti-mouse immunoglobulins antibody (R0439 from Agilent Dako, diluted 1:200 in PBS) for 30 min on ice. After three washing steps with PBS 10% mouse serum was added and incubated for 10 min on ice. Without further washing directly labelled antibodies against CD14, CD11b, CD16 and CD20 were added for 20 min on ice. After 2 washing steps with 0.9% NaCl red blood cells were lysed with Lysing Solution (BDBioscience) for 10 min in the dark. Cells were washed once with PBS and analyzed by flow cytometry to identify CD16-positive and CD16-negative monocytes. Mean fluorescence intensity for PE was determined for these cell populations and is depicted.

Figure 3:
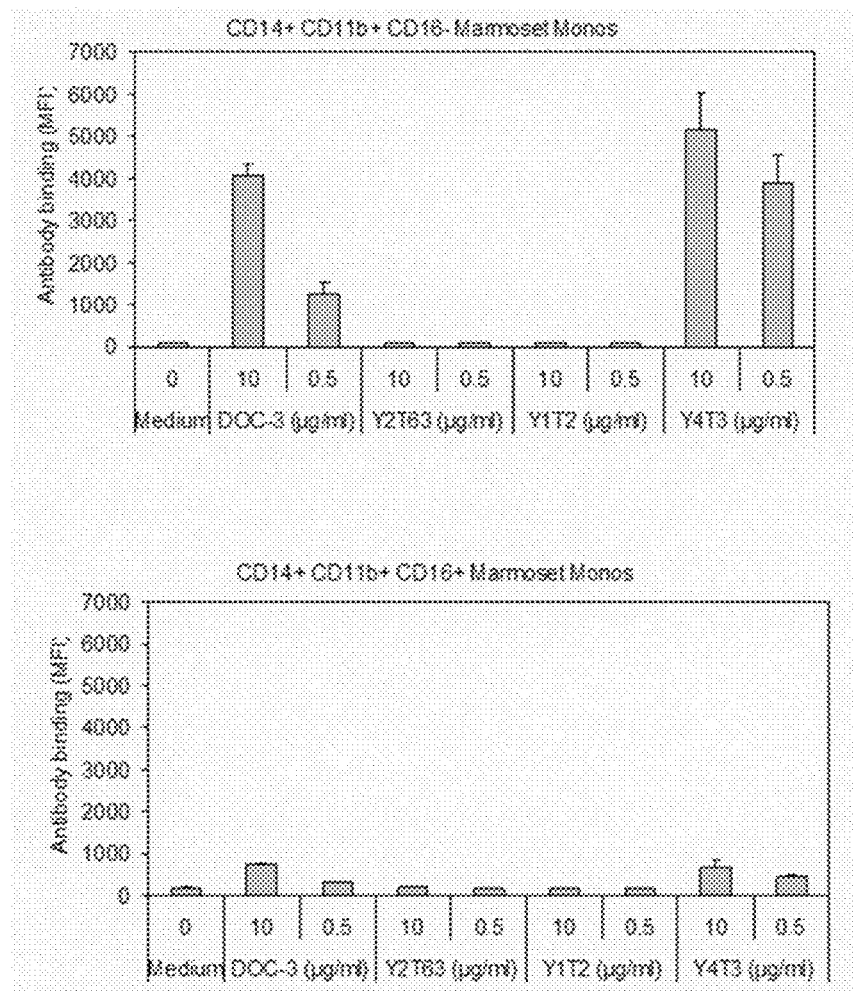
FIG. 3 demonstrates the binding of antibody Y4T3 to CD16-negative marmoset monocytes (top), but not to CD16-positive marmoset monocytes (bottom). Antibodies Y1T2 and Y2T63 do not bind to CD16-negative and CD16-positive marmoset monocytes.

Results are shown in FIG. 3. Exemplary antibodies DOC-3 and Y4T3 demonstrated binding to CD16-negative marmoset monocytes, but not to CD16-positive marmoset monocytes. Antibodies Y1T2 and Y2T63 did neither bind to CD16-negative, not to CD16-positive marmoset monocytes.

Antibody Y4T3 did not bind to CCR2 of cynomolgus monkeys (data not shown). CCR2 of cynomolgus monkeys, rhesus monkeys and Janaver have an identical amino acid sequence in the extracellular regions.

Example 5: Binding of Y4T3 to the ECL2 Domain of Human CCR2

To further investigate the specificity of the antibodies of the present invention, binding of Y4T3 to various CCR2 constructs was tested. Also tested were antibodies 1D9 and Clone 48607 (see above). CHO cells were stably transfected with the CCR2 constructs shown in Table 1. Untransfected CHO cells (empty) were also analyzed. Antibodies were tested at concentration of 10 µg/ml and incubated with the cells for 30 min on ice. After 3 washing steps with cold PBS, the bound antibodies were detected with a PE-labeled polyclonal rabbit anti-mouse immunoglobulins antibody (R0439 from Agilent Dako, diluted 1:200 in PBS) for 30 min on ice. After two washing steps with PBS, cells were analyzed by flow cytometry. Mean fluorescence intensity for PE was determined on cells and is depicted.

The following constructs were tested:

TABLE 1

| Construct | SEQ ID No. |
| --- | --- |
| Human CCR2b (hCCR2b) | 1 |
| Marmoset CCR2b (Marmo-CCR2b) | 3 |
| Rhesus CCR2b (rh-CCR2B) | 4 |
| Human CCR2b with the ECL2 domain of CCR2b of rhesus monkey (ECL2-hCCR2b) | 7 |
| Human CCR2b with ECL3 domain of CCR2b of of rhesus monkey (ECL2-hCCR2b) | 8 |
| Human CCR2b with the N-terminus of CCR2b of rhesus monkey (ECL2-hCCR2b) | 9 |

Figure 4:
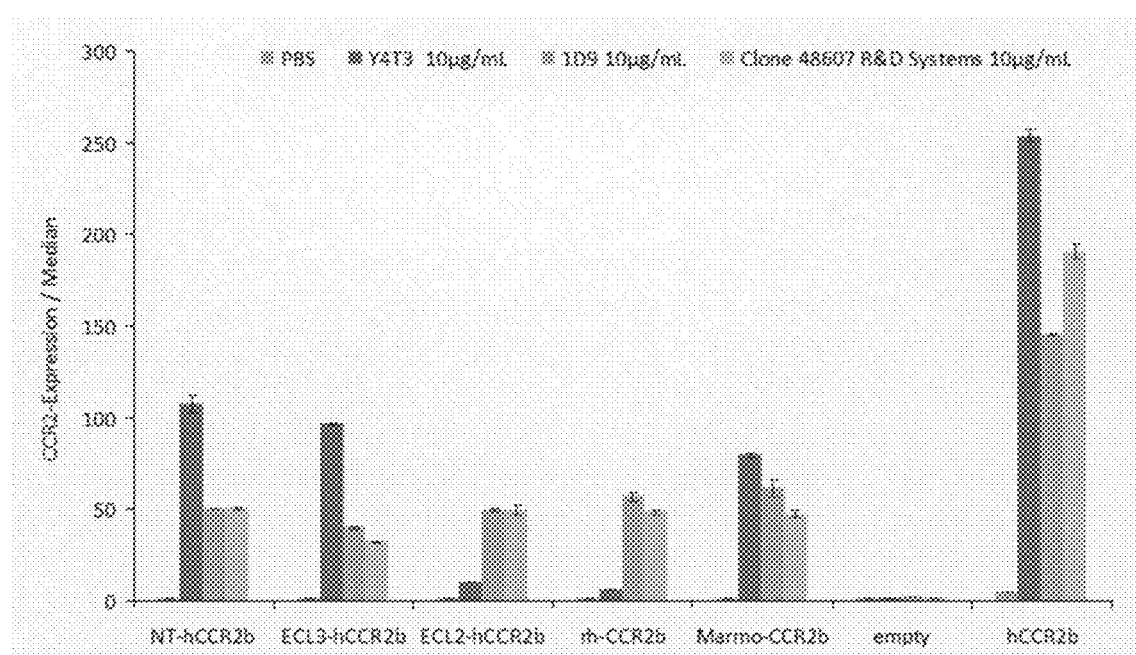
FIG. 4 shows that the ECL2 domain of human CCR2 is crucial for bind of Y4T3. Y4T3 did not bind to a variant of human CCR2b in which the ECL2 domain was replaced with the ECL2 domain of rhesus CCR2b.

Results are shown in FIG. 4. Antibody Y4T3 did bind to human CCR2b and to marmoset CCR2b, but not to rhesus CCR2b. Antibody Y4T3 did also bind to a human CCR2b variant in which the ECL3 domain was replaced with the ECL3 domain of rhesus CCR2b, and to a human CCR2b variant in which the N-terminus of CCR2b was replaced with the N-terminus of rhesus CCR2b. Antibody Y4T3 did no longer bind to a human CCR2b variant in which the ECL2 domain was replaced with the ECL2 domain of rhesus CCR2b. The ECL2 domain therefore contains amino acid residues that are crucial for binding of Y4T3. In contrast, antibodies 1D9 and Clone 48607 both also demonstrated reactivity with rhesus CCR2b.

Example 6: MCP-1 Induced Downregulation of CCR2 from the Surface of Human Monocytes Results in Reduced Binding of Y4T3 to Human Monocytes To investigate if binding of Y4T3 to human monocytes decreases when CCR2 is downregulated from the cell surface with MCP-1 the following experiment was performed. Human PBMC were preincubated with various concentrations of human MCP-1 (Peprotec) for 30 minutes at 37° C. Thereafter cells were cooled down to 4° C. and Y4T3 was added at 10 µg/ml for 30 min on ice. After 3 washing steps with cold PBS, the bound antibody was detected with a PE-labeled polyclonal rabbit anti-mouse immunoglobulins antibody (R0439 from Agilent Dako, diluted 1:200 in PBS) for 30 min on ice. After two washing steps with PBS, cells were analyzed by flow cytometry and monocytes were identified by light scatter properties. Mean fluorescence intensity for PE was determined on monocytes and is depicted.

Figure 5:
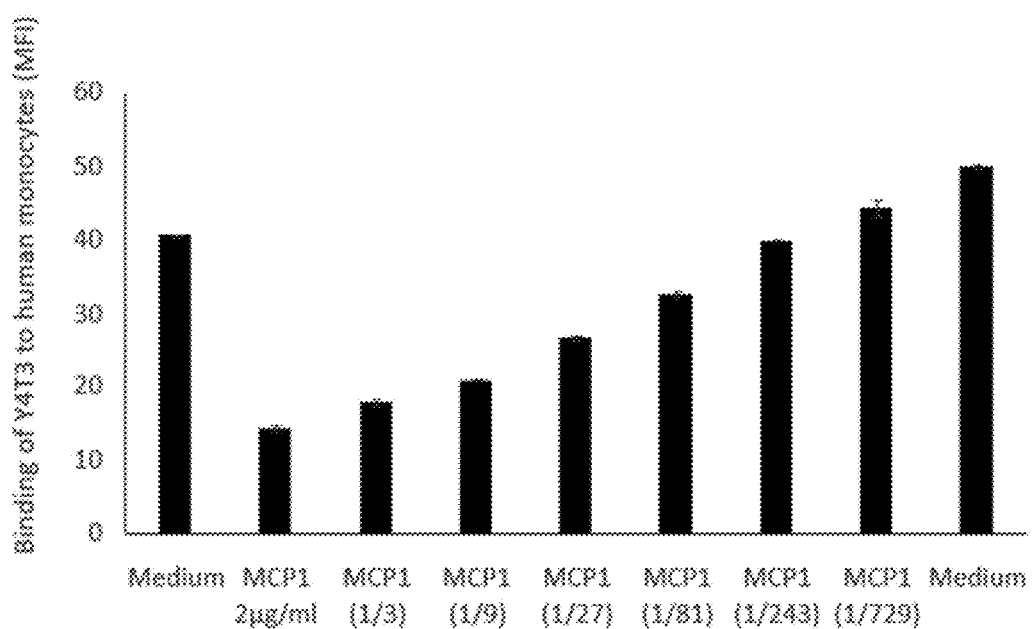
FIG. 5 demonstrates that downmodulation of human CCR2 with MCP-1 for 30 min at 37° C. reduces the binding of Y4T3 to human monocytes.

Results are shown in FIG. 5. At a concentration of 2 µg/ml MCP-1 more than 70% of the surface CCR2 signal obtained with Y4T3 was lost. Surface CCR2 signal returned when lower concentrations of MCP-1 were used.

This experiment demonstrates that Y4T3 binds to surface molecules that can be downregulated with MCP-1.

Example 7: Selection of a Candidate Antibody for Humanization

Based on the experimental data obtained so far a candidate antibody for humanization was selected. An overview of the properties of the lead antibodies is shown in the following table.

TABLE 2

| Property | Y4T3 Mouse BALB/c IgG1 kappa | Y2T63 Mouse BALB/c IgG1 kappa | Y1T2 Mouse BBALB/c IgG2a kappa |
|---|---|---|---|
| Isotype | | | |
| affinity to CCR2 expressed on human PBMCs | Excellent | good | good |
| affinity to CCR2 expressed on marmoset PBMCs | Excellent | No binding | No binding |
| affinity to CCR2 expressed on Janaver monocytes | No binding | Medium | good |
| Binding to human CCR5 | No binding | No binding | No binding |
| Binding domain | ECL2 | Not tested | Not tested |
| Blocking of MCP-1 induced downmodulation of CCR2 on human PBMCs | Yes | Not tested | Not tested |

Based on the experimental data available antibody Y4T3 was elected for humanization. Criteria included the high affinity of the binder to CCR2 on human PBMCs, as well as excellent cross-reactivity of the binder to marmoset CCR2.

Example 8: Humanization of Y4T3

Y4T3 was humanized by CDR-grafting resulting in hY4T3. Databases of Human IgG sequences and human germline sequences were searched for comparison to the murine VH domain and VL domain using BLAST search algorithms, and candidate human variable domains selected from the top 200 BLAST results. These were reduced to five candidates for VH (HC1-HC5 or H1-H5) and five candidates for VL (LC1-LC5 or L1-L5) based on a combination of framework homology, maintaining key framework residues and canonical loop structure. In total 25 humanized variants of Y4T3 were generated. The humanized Y4T3 variants were tested for binding to human CCR2+ monocytes in whole human blood by flow cytometry. 0.60 μl of lithium-heparin anticoagulated human whole blood was incubated for 45 min on ice with the indicated antibodies at 0.5 μg/ml in PBS. After three washing steps with cold PBS the bound antibodies were detected with PE-F(ab)2 goat anti human IgG (Jackson ImmunoResearch, 109-116-098) together with directly labeled antibodies against CD8, CD4, CD123 and CD116. After 2 washing steps with 0.9% NaCl red blood cells were lysed with Lysing Solution (BDBioscience) for 10 min in the dark. Cells were washed once with PBS and analyzed by flow cytometry to identify CCR2 expression on various cell types including monocytes. Mean fluorescence intensity (MFI) for PE was determined for these cell populations and is depicted.

Figure 6:
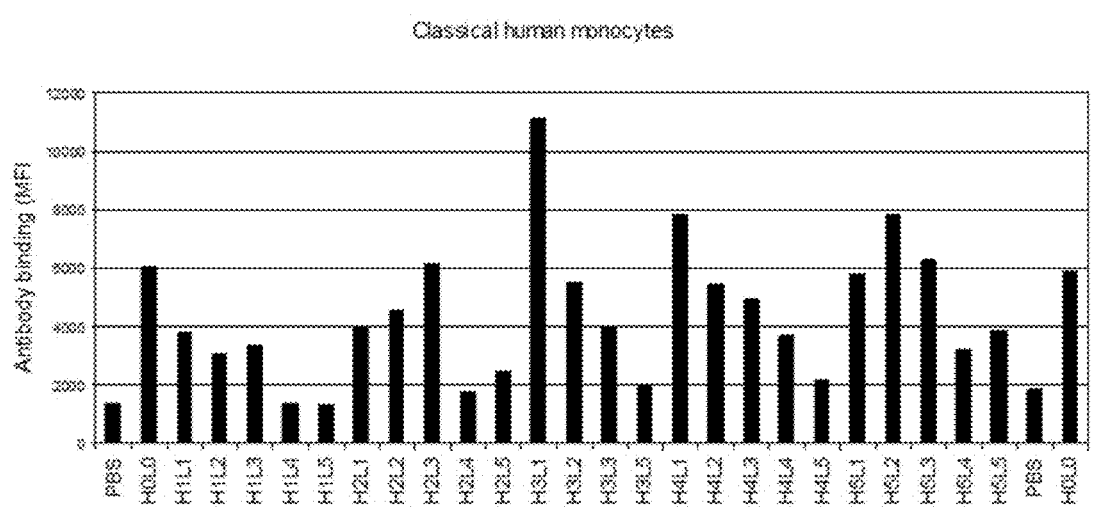
FIG. 6 shows binding of humanized variants of Y3T3 to CCR2 expressed on human monocytes. All antibodies were tested at 0.5 µg/ml. H0L0 designates the human IgG1 chimeric version of Y4T3. H1L1-H5L5 are the humanized variants of Y4T3.

Results are shown in FIG. 6. The majority of binders were able to bind to CCR2 expressed on human monocytes.

The binder selected, H3L1, showed a superior binding to CCR2-positive monocytes, but also other CCR2-positive cells like basophils, pDCs, and T cells. The selected binder is referred to as hY4T3.

Example 9: Sequence Determination of Y4T3 and hY4T3

Sequences of Y4T3 and hY4T3 were determined by standard sequencing technologies.

The variable heavy and the variable light chains, as well as the CDR regions according to Kabat and according to IMGT nomenclature are shown in the table below

TABLE 3

| SEQ ID No. | Description | Sequence |
|---|---|---|
| 24 | Y4T3 VH | MERHWIFLLLLSVTAGVHSQVHLQQSGTELA RPGASIKLSCKTSGSTFTRYTMHWIKQRPGQ GLEWIGFIVPSTGYTKYNQKFKDKATLTADK SSSTAYMHLNSLTSEDSALYYCARNKEVDYG ASWGQGTLVTVSA |
| 25 | Y4T3 VL | MSPAQFLFLLVLWIRVSEINGDVVMTQSPLT LSVTIGQPASISCKSSQSLLDSDGRTYLNWL LQRPGQSPKRLIYLVSKLDSGVPDRFTGSGS GTDFTLKISRVEAEDLGLYYCWQGSHFPQTF GGGTKLEIK |
| 22 | hY4T3 VH | QVQLVQSGAEVKKPGASVKVSCKASGSTFTR YTMHWVRQAPGQRLEWIGFIVPSTGYTKYNQ KFKDRVTITRDTSASTAYMELSSLRSEDTAV YYCARNKEVDYGASWGQGTLVTVSS |
| 23 | hY4T3 VL | DVVMTQSPLSLPVTLGQPASISCKSSQSLLD SDGRTYLNWFQQRPGQSPRRLIYLVSKLDSG VPDRFSGSGSGTDFTLKITRVEAEDVGVYYC WQGSHFPQTFGQGTKVEIK |
| 10 | hY4T3 HCDR1 Kabat | RYTMH |
| 11 | hY4T3 HCDR2 Kabat | FIVPSTGYTKYNQKFKD |
| 12 | hY4T3 HCDR3 Kabat | NKEVDYGAS |
| 13 | hY4T3 LCDR1 Kabat | KSSQSLLDSDGRTYLN |
| 14 | hY4T3 LCDR2 Kabat | LVSKLDS |
| 15 | hY4T3 LCDR3 Kabat | WQGSHFPQT |
| 16 | hY4T3 HCDR1 IMGT | GSTFTRYT |
| 17 | hY4T3 HCDR2 IMGT | IVPSTGYT |
| 18 | hY4T3 HCDR3 IMGT | ARNKEVDYGAS |
| 19 | hY4T3 LCDR1 IMGT | QSLLDSDGRTY |
| 20 | hY4T3 LCDR2 IMGT | LVS |
| 21 | hY4T3 LCDR3 IMGT | WQGSHFPQT |

The closest germline to the variable heavy chain of hY4T3 is IGHV1-3*01. The closest germline gene to the variable light chain of hY4T3 is IGKV2-30*01. See Table 4.

Table 4:

TABLE 4

| SEQ ID No. | Description | Sequence |
|---|---|---|
| 26 | IGHV1-3*01 | QVQLVQSGAEVKKPGASVKVSCKAS GYTFTSYAMHWVRQAPGQRLEWMGW INAGNGNTKYSQKFQGRVTITRDTS ASTAYMELSSLRSEDTAVYYCAR |
| 27 | IGKV2-30*01 | DVVMTQSPLSLPVTLGQPASISCRS SQSLVYSDGNTYLNWFQQRPGQSPR |

TABLE 4-continued

| SEQ ID No. | Description | Sequence |
| --- | --- | --- |
| | | RLIYKVSNRDSGVPDRFSGSGSGTD |
| 5 | | FTLKISRVEAEDVGVYYCMQGTHWP |

Compared to the closest germline sequence, the variable heavy chain of hY4T3 differs by one amino acid. In framework region 2, a methionine residues is replaced by an isoleucine residue to reduce oxidation. Similarly, in framework region 3 of the variable light chain, a serine residue is replaced by a threonine residue.

Example 10: hY4T3 Binds to CCR2+ Human Monocytes

Figure 7:
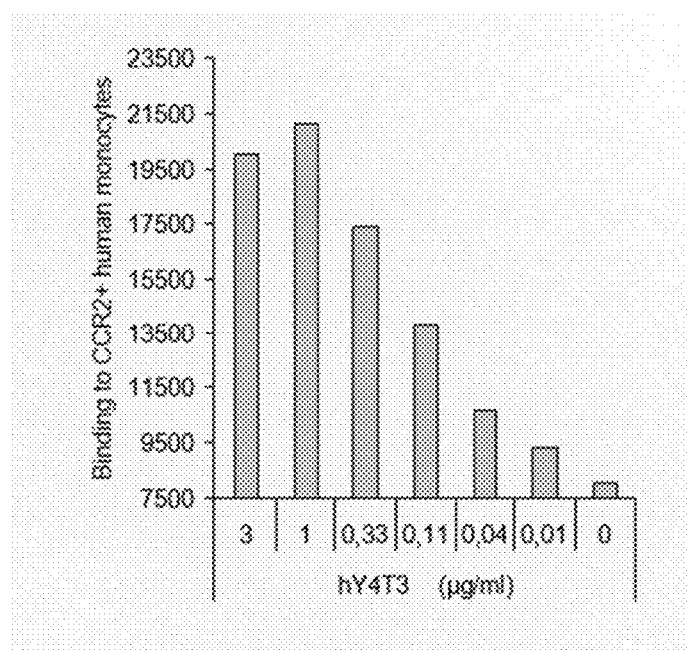
FIG. 7 demonstrates the binding of antibody hY4T3 to CCR2+ human monocytes. Concentration of the antibodies used is indicated on the x-axis.

Binding of hY4T3 to CCR2+ human monocytes was tested with human PBMC by flow cytometry. Human PBMCs were incubated for 30 min on ice with various concentrations of hY4T3 in PBS. After three washing steps with cold PBS the bound antibodies were detected with PE-F(ab)2 goat anti human IgG (Jackson ImmunoResearch, 109-116-098). After 3 washing steps with PBS 5% mouse and 5% rat serum was added for 10 min on ice. Without washing directly labeled antibodies against CD20, CD14, CD11b, CD16 were added. After 2 washing steps with 0.9% NaCl red blood cells were lysed with Lysing Solution (BDBioscience) for 10 min in the dark. Cells were washed once with PBS and analyzed by flow cytometry to identify CCR2 expression on monocytes. Mean fluorescence intensity (MFI) for PE was determined and is depicted. hY4T3 retained the property of binding to human monocytes. Results are shown in FIG. 7.

Example 11: hY4T3 Binds to CCR2+ Marmoset Monocytes

Figure 8:
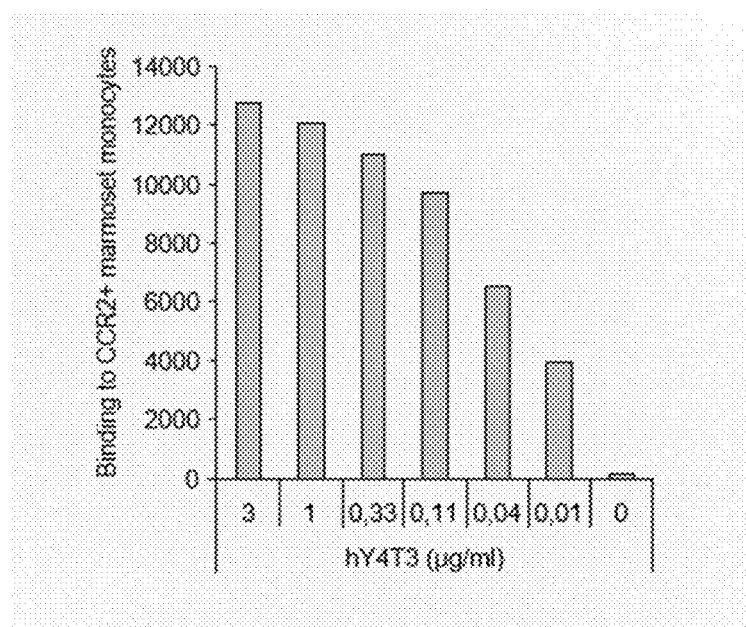
FIG. 8 demonstrates the binding of antibody hY4T3 to CCR2+ marmoset monocytes. Concentration of the antibodies used is indicated on the x-axis.

Binding of hY4T3 to CCR2+ marmoset monocytes was tested with marmoset splenocytes as described in Example 10. hY4T3 retained the property of binding to marmoset monocytes. Results are shown in FIG. 8.

Example 12: hY4T3 does not Bind to CCR5 Expressed in Transfected CHO Cells

Figure 9:
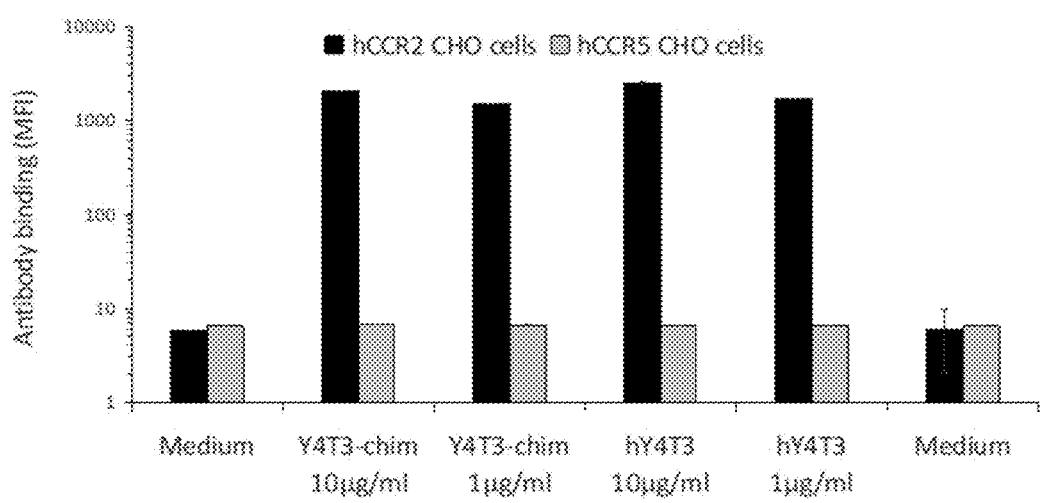
FIG. 9 shows binding of a human IgG1 chimeric variant of Y4T3 (Y4T3-chim) and of hY4T3 to CHO cells transfected with human CCR2. Y4T3-chim and hY4T3 do not bind to CHO cells transfected with human CCR5. Concentration of the antibodies used is indicated on the x-axis.

Like Y4T3, also a human IgG1 chimeric variant of Y4T3 (Y4T3-chim) and hY4T3 do not bind to CHO cells transfected with human CCR5. Y4T3-chim and hY4T3 do bind to CHO cells transfected with human CCR2. Antibodies were tested at concentration of 10 μg/ml and 1 μg/ml and incubated with the cells for 45 min on ice. After 3 washing steps with cold PBS, the bound antibodies were detected with PE-F(ab)2 goat anti human IgG (Jackson ImmunoResearch, 109-116-098) for 30 min on ice. After two washing steps with PBS, cells were analyzed by flow cytometry. Mean fluorescence intensity (MFI) for PE was determined and is depicted. Results are shown in FIG. 9.

Example 13: hY4T3 Blocks MCP-1 Induced Down-Regulation of CCR2 in Leukocytes To investigate the functional activity of hY4T3, the MCP-1 induced down-regulation of CCR2 was measured in various leukocyte subsets. Tested were basophils, plasmacytoid dendritic cells and CD16 low monocytes.

Cells were first incubated with hY4T3, MCP-1 or medium (RPMI) at various concentrations for 30 minutes at 37° C. Thereafter MCP-1, hY4T3 or RPMI was added, followed by another incubation for 30 minutes at 37° C. Cells were not washed between the first and the second incubation step. Cells were washed 3 times with PBS after the second incubation. Surface bound antibodies were detected with PE-F(ab)2 goat anti human IgG (Jackson ImmunoResearch, 109-116-098) together with directly labeled antibodies against CD3, CD8, CD4, CD123, CD304, CD116 and CD16. After 2 washing steps with 0.9% NaCl red blood cells were lysed with Lysing Solution (BDBioscience) for 10 min in the dark. Cells were washed once with PBS and analyzed by flow cytometry to identify CCR2 expression on various cell types including basophils, plasmacytoid dendritic cells and CD16low monocytes. Mean fluorescence intensity (MFI) for PE was determined for these cell populations and is depicted.

Figure 10:
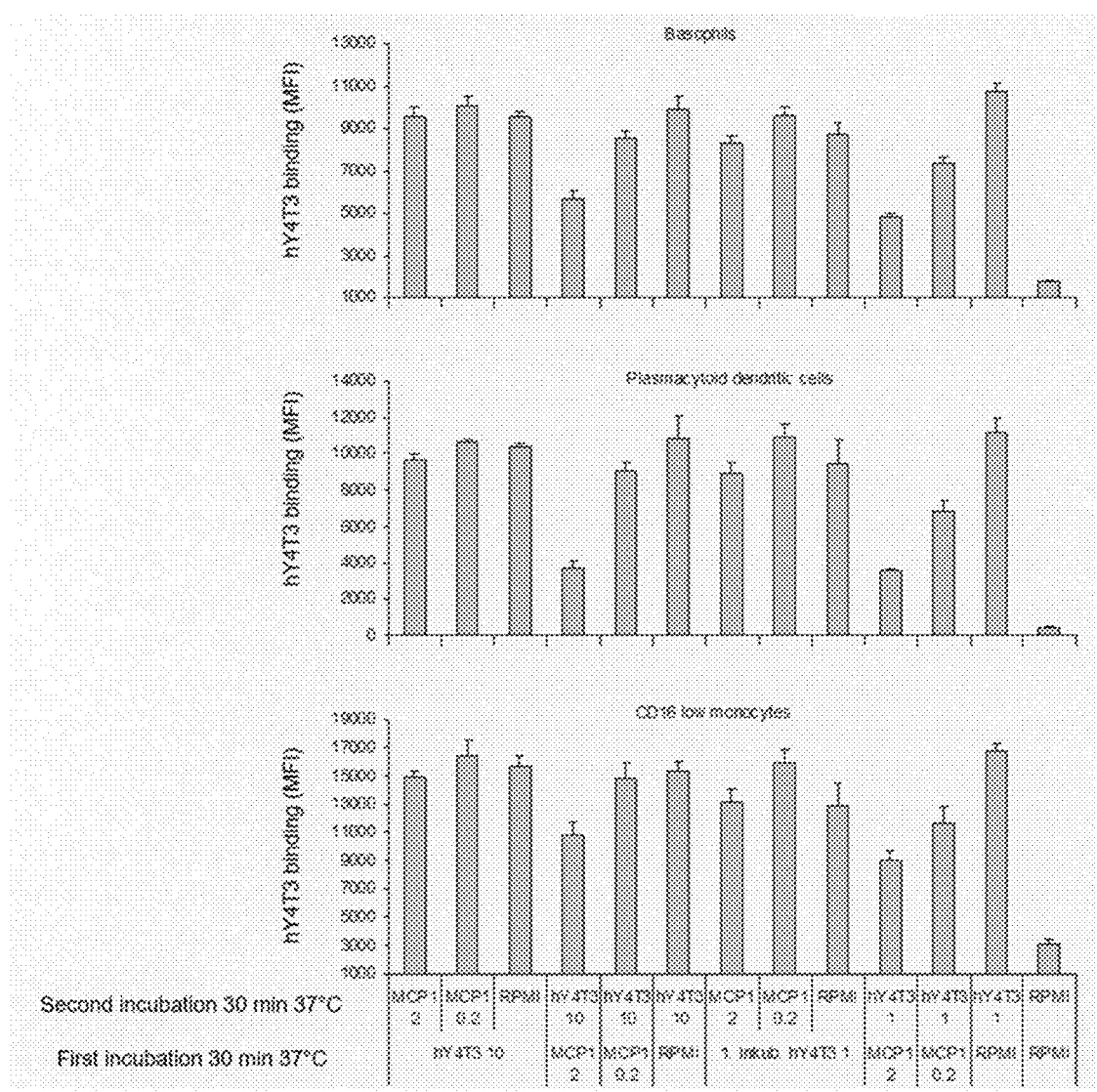
FIG. 10 demonstrates the blocking of MCP-1 induced downregulation of CCR2 by hY4T3 in various leukocyte subsets. Cells were first incubated with hY4T3, MCP-1 or medium (RPMI) at various concentrations as indicated (in µg/ml) for 30 minutes at 37° C. Thereafter MCP-1, hY4T3 or RPMI was added, followed by another incubation for 30 minutes at 37° C. Cells were not washed between the first and the second incubation step. Surface bound hY4T3 was detected with a PE-labeled goat anti-human IgG antibody.

Results are shown in FIG. 10. Pre-incubation with MCP-1 led to a decreased binding of hY4T3 to CCR2 in a dose-dependent manner. When cells were first incubated with hY4T3, the binding intensity was pretty much unaffected by a subsequent incubation with MCP-1.

This shows that hY4T3 blocks MCP-1 induced down-regulation of CCR2 in leukocytes, indicating that hY4T3 blocks activation of CCCR2 by MCP-1.

Example 14: Depletion of Cells in Marmosets Treated with hY4T3

Marmoset monkeys were treated with 5 mg/kg hY4T3 at time point 0 by slow intravenous injection. At various time points pre- and post-treatment whole blood was analyzed by flow cytometry. Whole blood anitcoagulated with EDTA was incubated for 30 min on ice with 3 μg/ml of hY4T3 in PBS. After three washing steps with cold PBS the bound antibodies were detected with PE-F(ab)2 goat anti human IgG (Jackson ImmunoResearch, 109-116-098) together with directly labeled antibodies against CD3, CD20, CD14, CD11b and CD16. After 2 washing steps with 0.9% NaCl red blood cells were lysed with Lysing Solution (BDBioscience) for 10 min in the dark. Cells were washed once with PBS and analyzed by flow cytometry to identify various cell populations. The experiment was performed with three monkeys.

Figure 11:
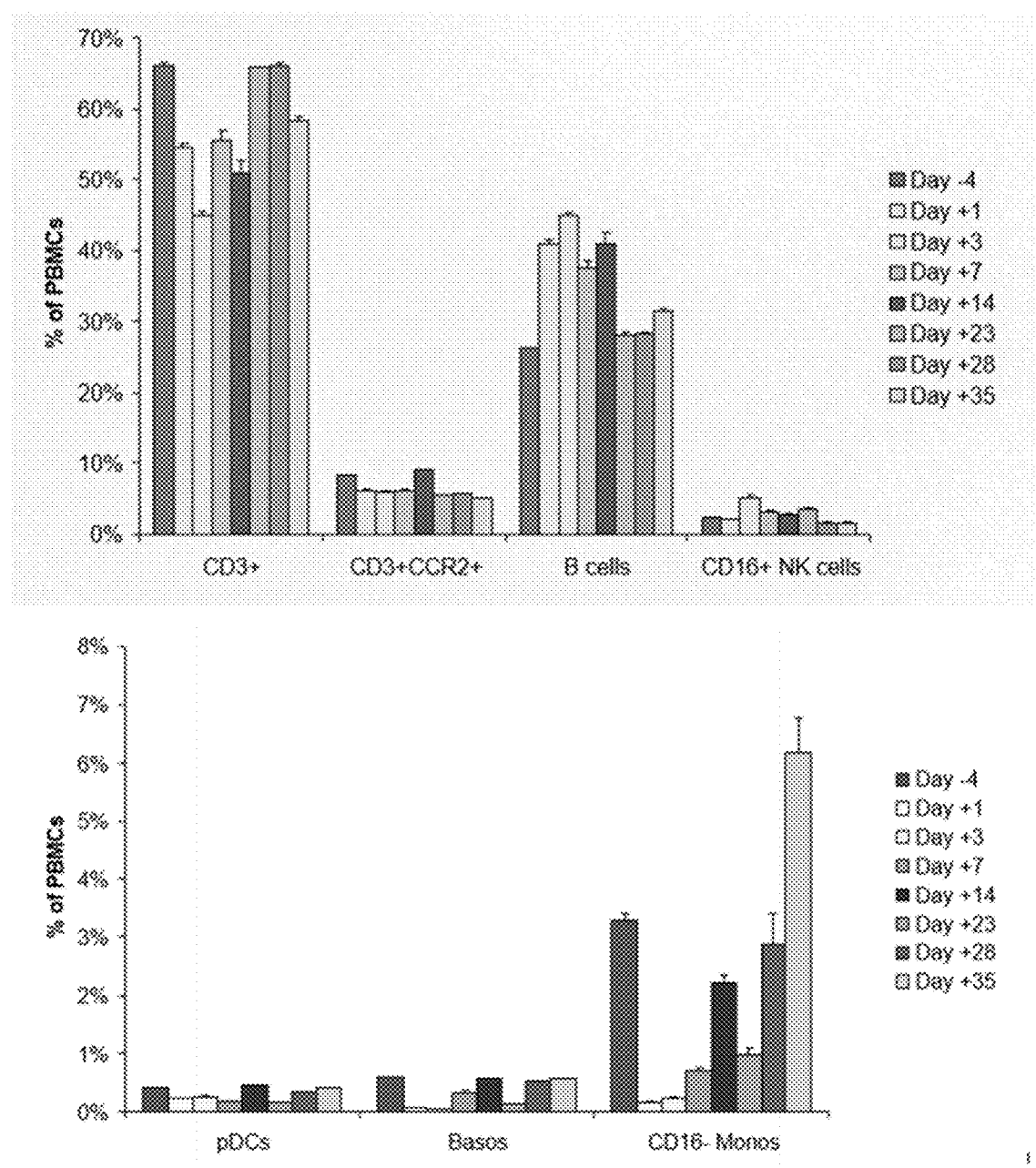
FIG. 11 shows the effect of treatment with hY4T3 on PBMCs from marmoset monkeys. Marmosets were treated with 5 mg/kg hY4T3 at time point 0. At various time points pre- and post-treatment leukocyte subpopulations were quantified in whole blood by flow cytometry. Relative cells counts are shown as % of PBMC.

Representative results for one monkey are shown in FIG. 11. The percentage of CD3-positive cell, CD3-positive/CCR2-positive cells, CD16-positive NK cell and plasmacytoid dendritic cells (pDCs) did not change significantly. The proportion of B cells increased upon treatment with hY4T3, but dropped back to the original level (i.e. the level pre-treatment) on day 23. The number of basophils strongly decreased upon treatment with hY4T3, but came back to the original level at about 1-2 weeks post treatment. The same pattern was observed for CD16-negative monocytes, which decreased strongly upon treatment with hY4T3. Numbers came back to original levels about 2 weeks post-treatment.

This shows that the antibodies and antibody fragments of the present disclosure are useful in the treatment of inflammatory diseases, autoimmune diseases, hematologic malignancies and potentially other diseases associated with expression of CCR2.

Example 15: Developability—hY4T3 has a Favorable Temperature Stability

To test if hY4T3 has a melting point indicative of a successful clinical development the melting point was measured by differential scanning calometry using a Microcal VP-DSC (Malvern). Temperature of a 8.44 mg/ml solution of hY4T3 in PBS plus 100 mM L-arginine was increased from 25-130° C. with a rate of 1° C. per minute.

The melting point of the CH2 domain was determined to be 70.9° C. (Tm1). The Fab domain and the CH3 domain have a melting point of 75.1° C. (Tm2). The complete melting of the molecule occurred at 82.5° C. (Tm3).

Figure 12:
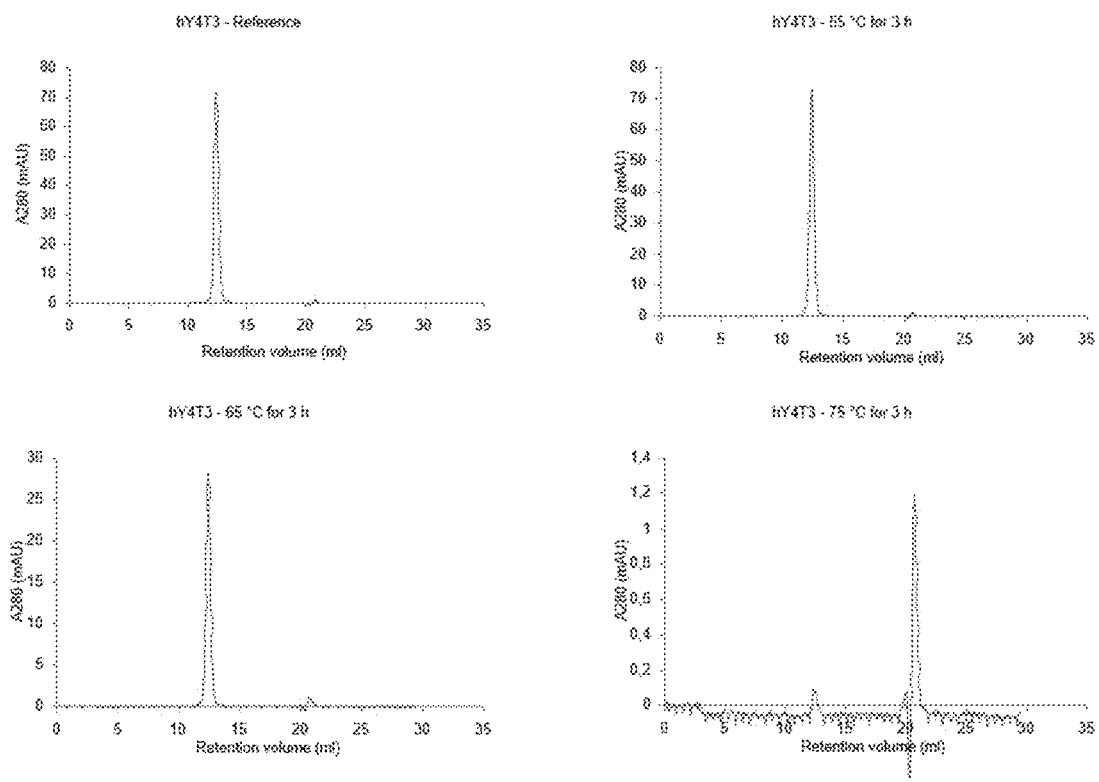
FIG. 12 shows SEC chromatograms for hY4T3 after incubation for 3 hours at the indicated temperatures (top left=reference; top right=55° C.; bottom left=65° C.; bottom right=75° C.).

Stability of hY4T3 was further investigated by analytical size-exclusion chromatography (SEC). A 8.44 mg/ml solution of hY4T3 in PBS plus 100 mM L-arginine was incubated for 3 hours at 55, 65 or 75° C., respectively, followed by analytical SEC using Superdex 200 Increase and photometric detection of proteins at 280 nm. Results are shown in FIG. 12. The SEC pattern of hY4T3 incubated at 55° C. for 3 hours was indistinguishable from the reference, i.e. the antibody kept at 4° C. After incubation for 3 hours at 65° C. more than 50% of the signal was lost due to generation of insoluble denatured proteins. At incubation of hY4T3 for 3 hours at 75° C. most of the antibody was lost due to generation of insoluble denatured proteins. There were almost no cleavage products or soluble aggregates.

Figure 13:
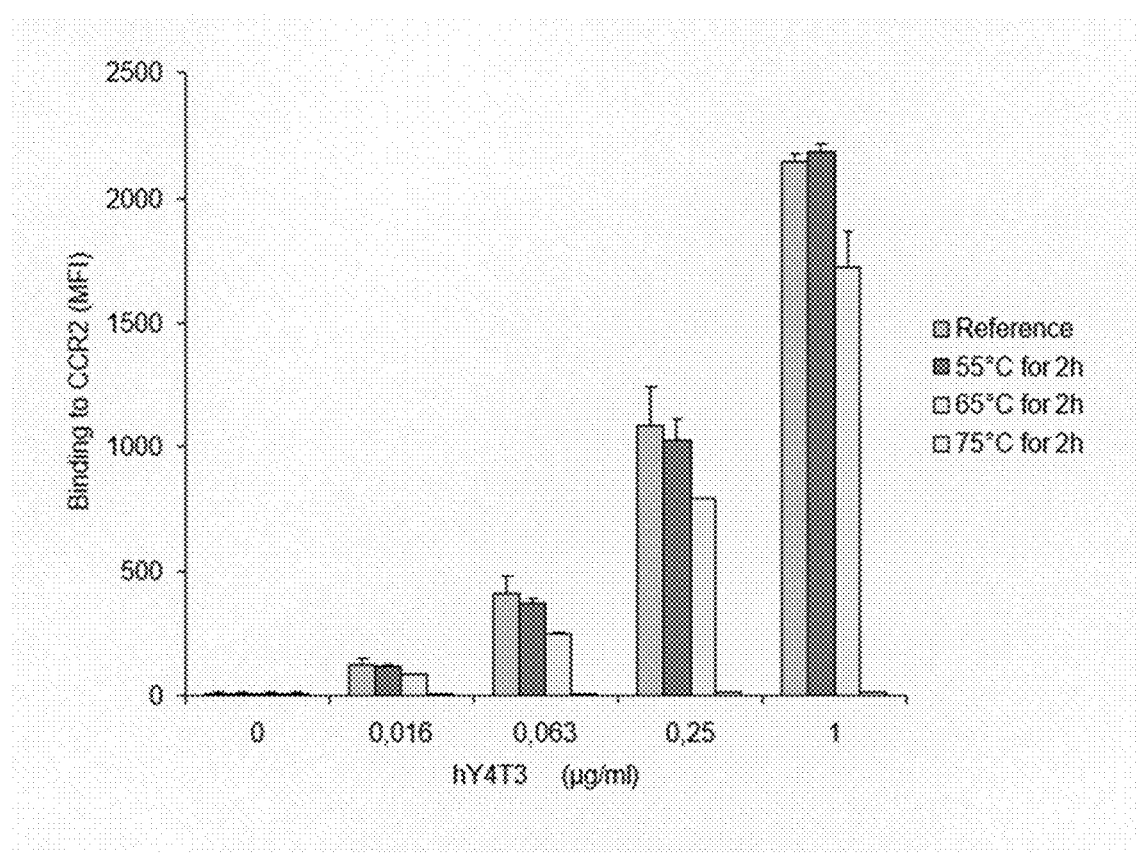
FIG. 13 shows the binding of hY4T3 to CCR2 on CHO cells, after incubation of the antibody for 2 hours at the indicated temperatures.

Binding of hY4T3 to CCR2 on CHO cells was likewise examined. A 8.44 mg/ml solution of hY4T3 in PBS plus 100 mM L-arginine was incubated for 2 hours at 55, 65 and 75° C., respectively. The antibody preparations were then tested for binding to CCR2 on CHO cells as described above. Results are shown in FIG. 13. hY4T3 incubated at 55° C. for 2 hours showed the same degree of binding to CHO cells as the reference, i.e. the antibody kept at 4° C. A slight loss of binding was observed after incubation for 2 hours at 65° C. Incubation of hY4T3 for 2 hours at 75° C. led to a loss of binding.

hY4T3 was also stable at 37° C. for at least 14 days (longest time point tested) at various antibody concentrations (0.015625, 0.0625, 0,25 and 1 μg/ml) in PBS as well as in serum (data not shown). These data indicate that the melting point of hY4T3 is very favorable, supporting a successful clinical development. The antibody is stable at least for 2 hours at 55° C.

Example 16: Developability—hY4T3 has a Favorable Freeze-Thaw Stability

To test the behavior of hY4T3 to repeated freezing and thawing, hY4T3 (8.44 mg/ml in PBS mit 100 mM L-arginine) was subjected to repeated freeze-thaw cycles. After ten cycles of freezing and thawing, the samples were subjected to SEC and no differences could be observed compared to the reference (data not shown).

Figure 14:
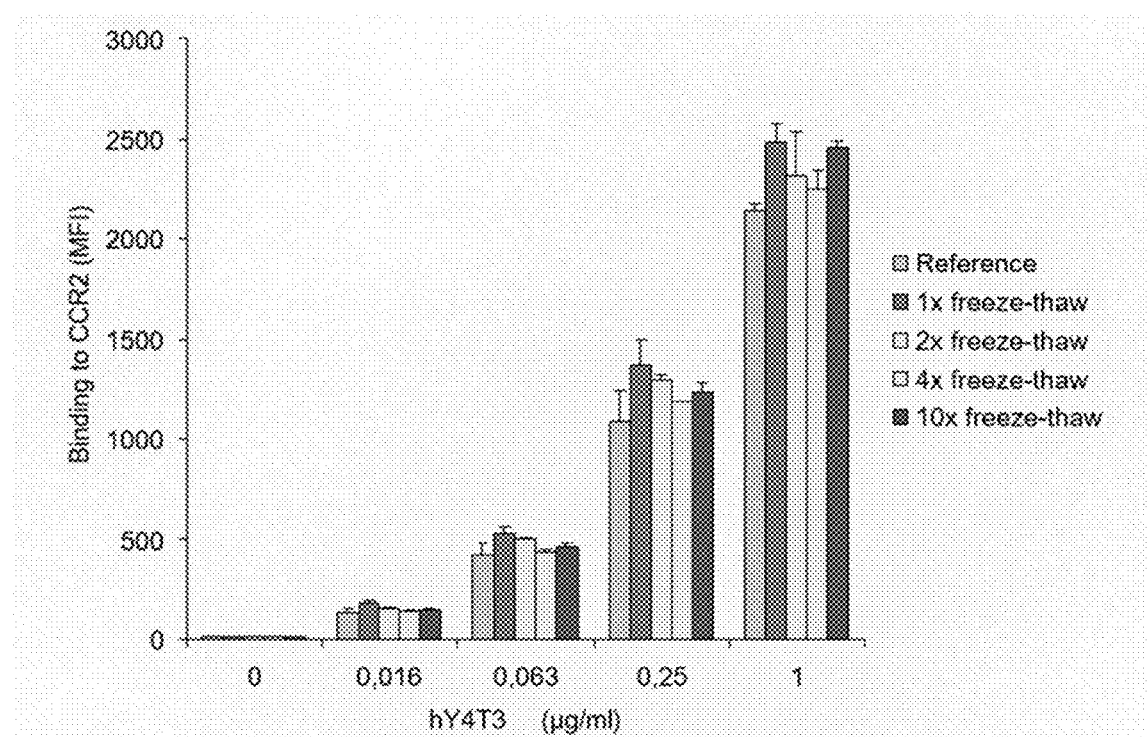
FIG. 14 shows the binding of hY4T3 to CCR2 on CHO cells, after repeated freeze-thaw cycles of the antibody preparation.

Samples of hY4T3 (8.44 mg/ml in PBS mit 100 mM L-arginine) were also tested for binding to CCR2 on CHO cells after various freeze-thaw-cycles. Results are shown in FIG. 14. Up to ten cycles of freezing and thawing, the preparations showed no loss of binding to CCR2 expressed on CHO cells.

These data further indicate that hY4T3 is stable, supporting a successful clinical development.

Example 17: Developability—hY4T3 is Stable Over a Broad pH Range

To test the behavior of hY4T3 at various pH ranges hY4T3 was incubated at various antibody concentrations for two hours in buffers of various pH's.

To do so, a 8.44 mg/ml solution of hY4T3 in PBS plus 100 mM L-arginine was dissolved 1:5 with water and the pH was adjusted to desired values with HCl/NaOH. Samples were then incubated at 2 hours at room temperature followed by a readjustment of the pH to 7.2 with HCl/NaOH.

Figure 15:
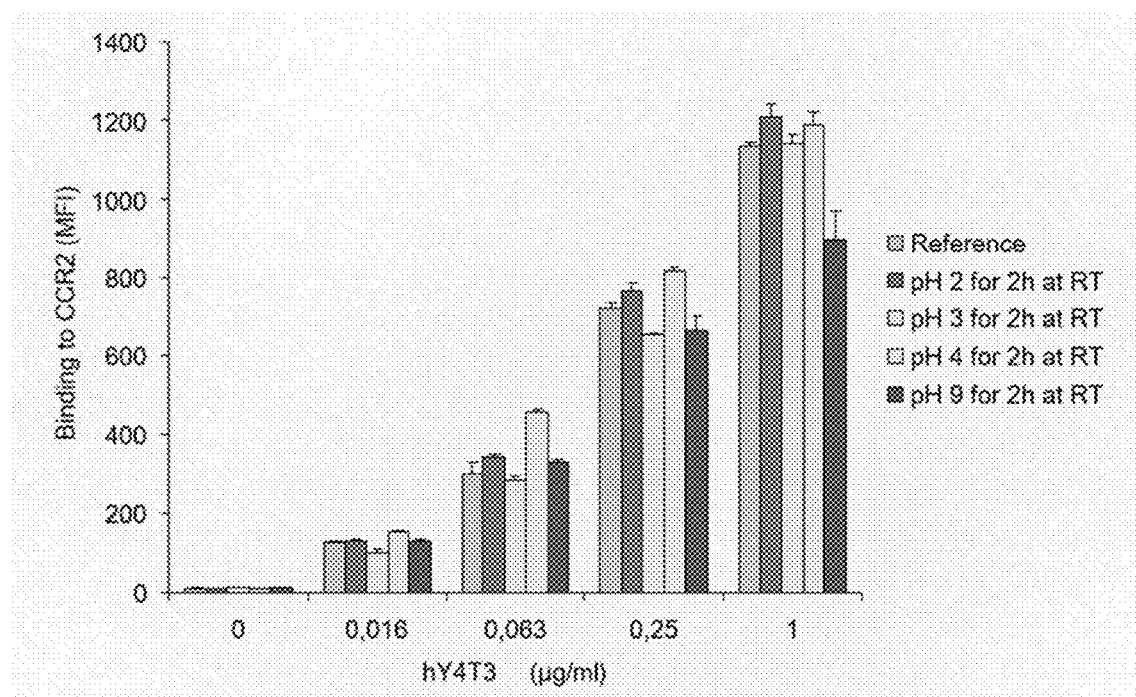
FIG. 15 shows the binding of hY4T3 to CCR2 on CHO cells, after incubation of the antibody at various antibody concentrations for 2 hours at the indicated pH's.

Binding of the samples to CCR2 expressed on CHO cells was measured using various concentrations of the pH exposed antibody. Results are shown in FIG. 15.

Compared to the reference sample (pH 6,82), incubation to a pH as low as 2 had no effect on binding to CCR2 expressed on CHO cells. Incubation at a pH of 9 showed a slight loss of binding.

Again, these data indicate that hY4T3 is highly stable even at a very low pH, again strongly supporting a successful clinical development. The antibody is stable for at least 2 hours at pH3.0 and 22° C.

Example 18: Developability—hY4T3 is Stable in Blood Plasma

To test the behavior of hY4T3 in plasma various experiments were performed. hY4T3 was incubated at various concentrations for 48 hours, 7 days and 14 days in PBS and human plasma.

Figure 16:
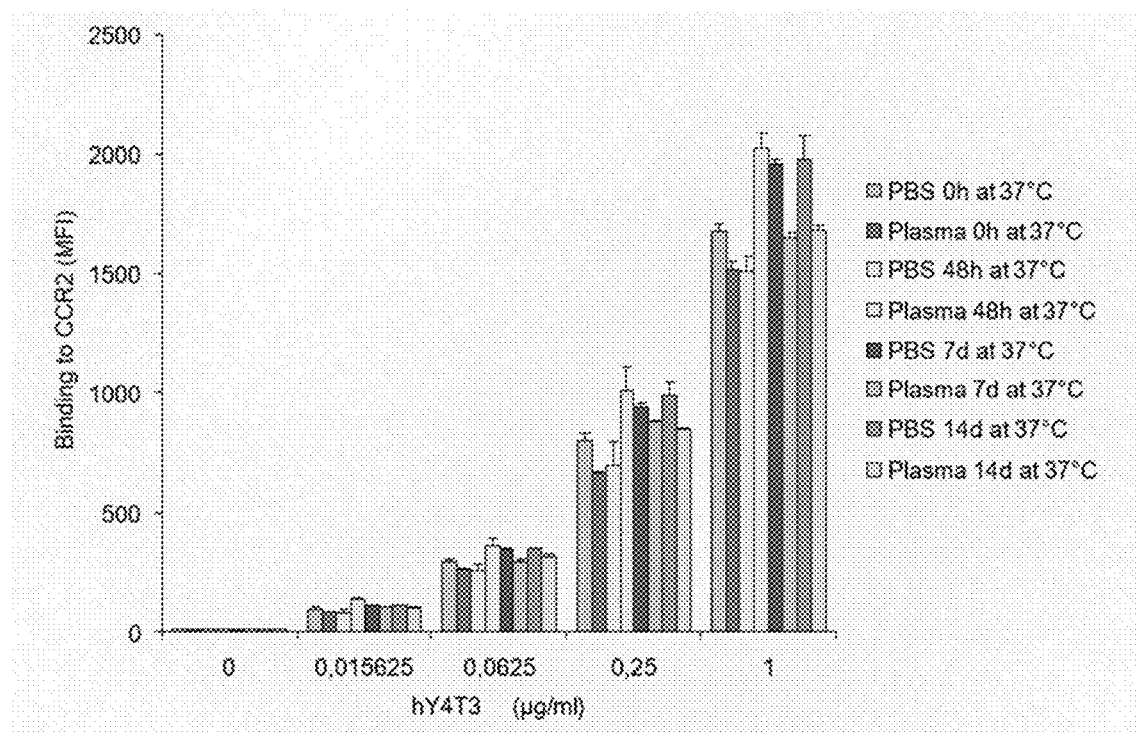
FIG. 16 shows the binding of hY4T3 to CCR2 on CHO cells, after incubation of the antibody for various time intervals in PBS and human plasma. The antibody was incubated at a concentration of 1 mg/ml for the indicated time intervals. Thereafter binding of the antibody was tested in various dilution.

To do so, 23.7 μl hY4T3 (8.44 mg/ml in PBS with 100 mM L-arginine) was mixed with 176.3 μl PBS or human lithium-heparin plasma (1 mg/ml) and incubated for 0 hours, 48 hours or 14 days at 37° C. Thereafter, binding of the samples to CCR2 expressed on CHO cells was measured using various concentrations of the exposed antibody. Results are shown in FIG. 16.

Binding to CCR2 expressed on CHO cells was not dependent on the time interval of incubation. There was also no difference between incubation in PBS and incubation in human plasma.

This experiment further confirms the advantageous biochemical properties of hY4T3.

Example 19: Comparison to Prior Art Antibodies

Antibody Y4T3 was compared to prior art antibodies DOC2, 1D9 (BDBioscience) and Clone 48607 (R&D Systems; Catalogue #: MAB150). The DOC-2 antibody has the following amino acid sequence:

VH:
(SEQ ID No. 28)
EVQLVESGGGLVKPGGSLKLSCVASGFTLSNYAMSWVRQSPEKRLEWVA
EVSSSGIYIYYSDTVTGRFSISRDNAKNTLYLEMSSLRSEDTAIYYCAR
DRYAYAMDYWGHGTSVIVSS

VL:
(SEQ ID No. 29)
DIVMTQSPSSLAISVGQRVTLSCKSSQSLLNSYNQKNSLAWYQQKPGQS
PKLLVYFASTRESGVPDRFIGSGSGTYFTLTITSVQAGDLADYFCQQHY
SNPRTFGGGTRLEIK

Human heparinized whole blood was incubated with the indicated antibodies for 45 min on ice, washed three times with cold PBS, then stained with secondary PE-labeled rabbit-anti-mouse Ig (R0439, DakoCytomation 1:200) for 30 min on ice, washed 3 times with cold PBS. The 10% mouse serum was added for 10 min and after that directly labeled antibodies against CD3-APCCy7, CD8-PE-Cy7, CD4-V500, CD123-PerCP, CD304-APC, CD116-FITC, CD16-PB. After washing and lysis of red blood cells with BD Lysing solution cells were aquired on a FACSCanto-II and analyzed by FACS-DIVA software. Classical monocytes were identified by light scatter properties, expression of CD116 and absence of CD16 and CD123. Median fluorescence intensity for PE is depicted on classical monocytes.

Figure 17:
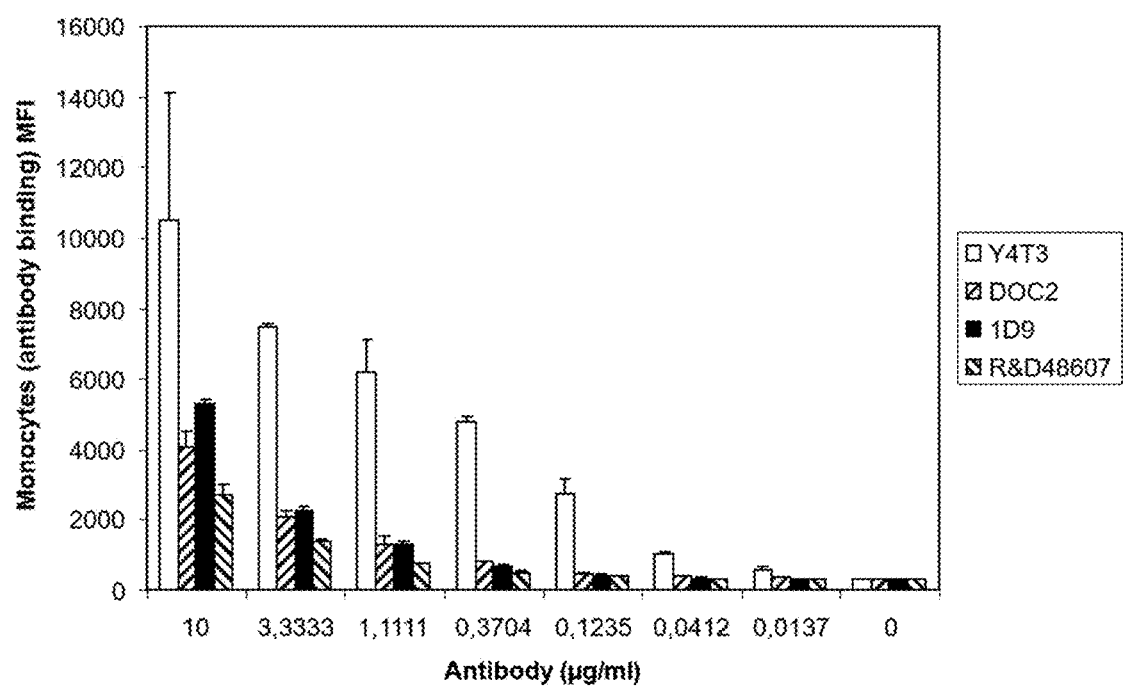
FIG. 17 shows a comparison of the binding of antibody Y4T4 to prior art antibodies DOC2, 1D9 and Clone 48607 on human monocytes.

Results are shown in FIG. 17. The affinity of Y3T3 was more than 5-fold higher than that of the tested prior art antibodies.

Example 20: hY4T3 does not Cross-React with Mouse CCR2

MouseCCR2 CHO cells and humanCCR2 CHO cells were incubated for 45 min on ice with PBS or various concentrations of MC-21 (rat monoclonal antibody against mouse CCR2; University of Regensburg). After 3 washing steps with cold PBS, cells were stained with Biotin-anti-rat IgG2b antibody (5 µg/ml; BD Clone RG7/11.1, Cat No. 553898) for 30 min on ice. After 3 washing steps with cold PBS, cells were stained with Streptavidin-PE (1:100) for 30 min on ice. After 3 washing steps with cold PBS cells were analyzed by FACS to measure mean fluorescence intensity (MFI).

Mouse CCR2 CHO cells and humanCCR2 CHO cells were incubated for 45 min on ice with PBS or various concentrations of hY4T3. After 3 washing steps with cold PBS, cells were stained PE-F(ab)2 goat anti human IgG (1:300; Jackson, Cat. No. 109-116-098) for 30 min on ice. After 3 washing steps with cold PBS cells were analyzed by FACS to measure mean fluorescence intensity (MFI).

Figure 18:
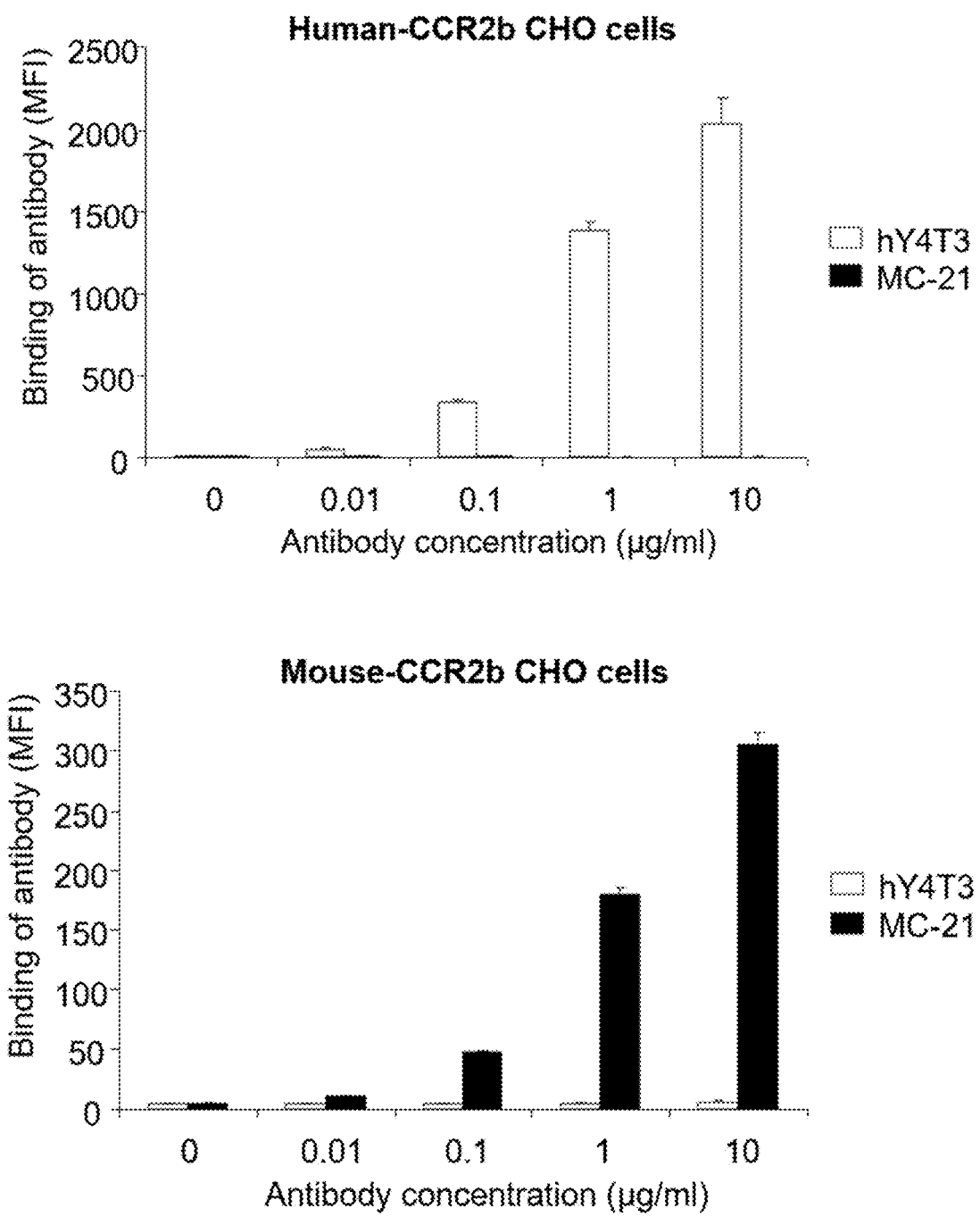
FIG. 18 shows that hY4T3 binds to human CCR2, but to mouse CCR2. MC-21 does bind to mouse CCR2, but not to human CCR2.

Results are shown in FIG. 18. hY4T3 does not bind to mouse CCR2. MC-21 does not bind to human CCR2.

Example 21: Antagonistic Effect of hY4T3, Efficiently Blocking Chemokine Receptor CCR2

The PathHunter® eXpress CCR2 CHO-K1 β-Arrestin GPCR Assay (DiscoverX; Cat #93-0192E2CPOM) was used to assess antagonistic activity of hY4T3 following manufacturer protocol. CCR2 CHO K1 β-Arrestin GPCR cells from the kit were thawed, seeded and incubated for 48 h at 37° C. and 5% C02. After the incubation, different concentrations of CCL2 (MCP-1), hY4T3, hY4T3 pre-incubated for 30 mins with fixed concentrations of CCL2 (EC20, EC50 and EC80) or hY4T3 pre-incubated for 30 min with an anti IgG antibody (Biorad; #MCA5748G) were prepared and added to the cells. After 90 mins incubation at 37° C. and 5% C02, detection reagent is added to the plate and luminescence was measured on the Envision plate reader after 60 min.

Figure 19:
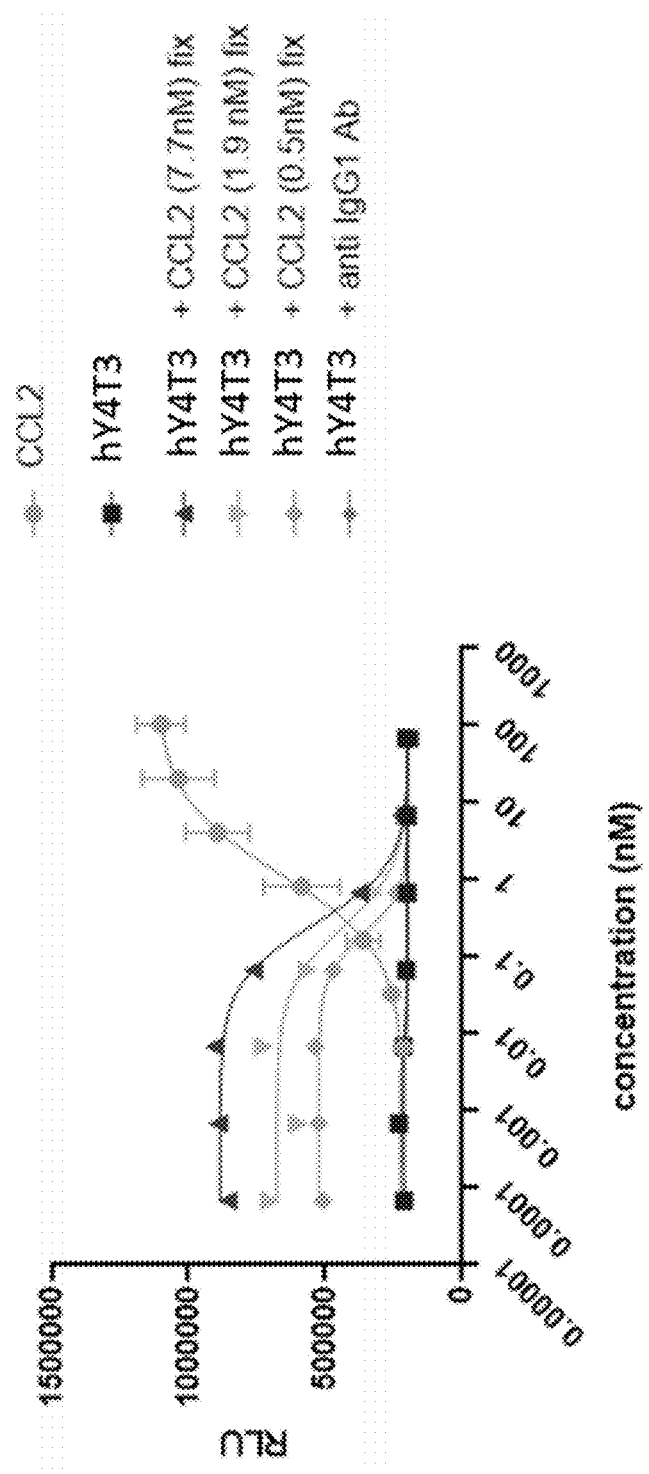
FIG. 19 shows that hY4T3 efficiently blocks chemokine receptor CCR2.

Results are shown in FIG. 19. This experiment demonstrates that hY4T3 is a potent CCR2 antagonist with no agonistic activity at any of the tested conditions.

The invention claimed is:

1. An antibody or antibody fragment that specifically binds to human CCR2, comprising a VH comprising HCDR1, HCDR2, and HCDR3, and a VL comprising LCDR1, LCDR2, and LCDR3, wherein the HCDR1, HCDR2, and HCDR3 comprise the HCDR1, HCDR2, and HCDR3 amino acid sequences of the VH amino acid sequence set forth in SEQ ID NO: 22; and wherein the LCDR1, LCDR2, and LCDR3 comprise the LCDR1, LCDR2, and LCDR3 of the VL amino acid sequence set forth in SEQ ID NO: 23.

2. The antibody or antibody fragment of claim 1, wherein the HCDR1, HCDR2, HCDR3, LCDR1, LCDR2, and LCDR3 comprise the amino acid sequences set forth in SEQ ID NO: 10, SEQ ID NO: 11, SEQ ID NO: 12, SEQ ID NO: 13, SEQ ID NO: 14, and SEQ ID NO: 15, respectively.

3. The antibody or antibody fragment of claim 1, wherein the HCDR1, HCDR2, HCDR3, LCDR1, LCDR2, and LCDR3 comprise the amino acid sequences set forth in SEQ ID NO: 16, SEQ ID NO: 17, SEQ ID NO: 18, SEQ ID NO: 19, SEQ ID NO: 20, and SEQ ID NO: 21, respectively.

4. The antibody or antibody fragment of claim 1, wherein the VH comprises the amino acid sequence set forth in SEQ ID NO: 22.

5. The antibody or antibody fragment of claim 1, wherein the VL comprises the amino acid sequence set forth in SEQ ID NO: 23.

6. The antibody or antibody fragment of claim 1, which is an antibody of the human IgG1 class.

7. The antibody or antibody fragment of claim 1, wherein the antibody or antibody fragment is cross-reactive with marmoset CCR2, but not rhesus CCR2.

8. The antibody or antibody fragment of claim 1, wherein the antibody or antibody fragment does not bind to human CCR5 (SEQ ID NO: 6).

9. An antibody or antibody fragment that specifically binds to human CCR2, comprising a VH comprising the amino acid sequence set forth in SEQ ID NO: 22, and a VL comprising the amino acid sequence set forth in SEQ ID NO: 23.

10. The antibody or antibody fragment of claim 9, which is an antibody of the human IgG1 class.

11. The antibody or antibody fragment of claim 9, wherein the antibody or antibody fragment is cross-reactive with marmoset CCR2, but not rhesus CCR2.

12. The antibody or antibody fragment of claim 9, wherein the antibody or antibody fragment does not bind to human CCR5 (SEQ ID NO: 6).

13. A nucleic acid sequence or plurality of nucleic acid sequences encoding a VH and/or a VL, or a heavy chain and/or a light chain of the antibody of claim 1.

14. A vector or plurality of vectors comprising the nucleic acid sequence or plurality of nucleic acid sequences of claim 13.

15. A host cell comprising the nucleic acid sequence or plurality of nucleic acid sequences of claim 13.

16. A method for producing an antibody or antibody fragment that specifically binds to CCR2, comprising culturing the host cell of claim 15 under conditions which permit expression of the antibody or antibody fragment.

17. A composition comprising the antibody or antibody fragment of claim 1 and at least one pharmaceutically acceptable carrier.

18. A method of blocking MCP-1-induced downregulation of CCR2 in a subject in need thereof comprising administering a therapeutically effective amount of the antibody or antibody fragment of claim 1 to the subject.

19. A method of treating a disease associated with undesired presence of CCR2 in a subject in need thereof comprising administering a therapeutically effective amount of the antibody or antibody fragment of claim 1 to the subject.

20. A method of treating an inflammatory disease or an autoimmune disease in a subject in need thereof comprising administering a therapeutically effective amount of the antibody or antibody fragment of claim 1 to the subject.

21. A method of treating a proliferative disease in a subject in need thereof comprising administering a therapeutically effective amount of the antibody or antibody fragment of claim 1 to the subject.

22. A nucleic acid sequence or plurality of nucleic acid sequences encoding a VH and/or a VL, or a heavy chain and/or a light chain of the antibody of claim 9.

23. A vector or plurality of vectors comprising the nucleic acid sequence or plurality of nucleic acid sequences of claim 22.

24. A host cell comprising the nucleic acid sequence or plurality of nucleic acid sequences of claim 22.

25. A method for producing an antibody or antibody fragment that specifically binds to CCR2, comprising culturing the host cell of claim 24 under conditions which permit expression of the antibody or antibody fragment.

26. A composition comprising the antibody or antibody fragment of claim 9 and at least one pharmaceutically acceptable carrier.

27. A method of blocking MCP-1-induced downregulation of CCR2 in a subject in need thereof comprising administering a therapeutically effective amount of the antibody or antibody fragment of claim 9 to the subject.

28. A method of treating a disease associated with undesired presence of CCR2 in a subject in need thereof comprising administering a therapeutically effective amount of the antibody or antibody fragment of claim 9 to the subject.

29. A method of treating an inflammatory disease or an autoimmune disease in a subject in need thereof comprising administering a therapeutically effective amount of the antibody or antibody fragment of claim 9 to the subject.

30. A method of treating a proliferative disease in a subject in need thereof comprising administering a therapeutically effective amount of the antibody or antibody fragment of claim 9 to the subject.

* * * * *

```
                          SEQUENCE LISTING

Sequence total quantity: 29
SEQ ID NO: 1            moltype = AA  length = 360
FEATURE                 Location/Qualifiers
source                  1..360
                        mol_type = protein
                        organism = Homo sapiens
SEQUENCE: 1
MLSTSRSRFI RNTNESGEEV TTFFDYDYGA PCHKFDVKQI GAQLLPPLYS LVFIFGFVGN   60
MLVVLILINC KKLKCLTDIY LLNLAISDLL FLITLPLWAH SAANEWVFGN AMCKLFTGLY  120
HIGYFGGIFF IILLTIDRYL AIVHAVFALK ARTVTFGVVT SVITWLVAVF ASVPGIIFTK  180
CQKEDSVYVC GPYFPRGWNN FHTIMRNILG LVLPLLIMVI CYSGILKTLL RCRNEKKRHR  240
AVRVIFTIMI VYFLFWTPYN IVILLNTFQE FFGLSNCEST SQLDQATQVT ETLGMTHCCI  300
NPIIYAFVGE KFRRYLSVFF RKHITKRFCK QCPVFYRETV DGVTSTNTPS TGEQEVSAGL  360

SEQ ID NO: 2            moltype = AA  length = 28
FEATURE                 Location/Qualifiers
source                  1..28
                        mol_type = protein
                        organism = Homo sapiens
SEQUENCE: 2
TKCQKEDSVY VCGPYFPRGW NNFHTIMR                                      28

SEQ ID NO: 3            moltype = AA  length = 359
FEATURE                 Location/Qualifiers
source                  1..359
                        mol_type = protein
                        organism = Callithrix jacchus
SEQUENCE: 3
MLSTSHSRFI RNTESGEEVT TIFDYDYGAP CHKFDVKQIG AQLLPPLYSL VFIFGFVGNM   60
LVVLILINCK KLKSLTDIYL LNLAVSDLLF LITLPLWAHS AANEWVFGNA VCKLFTGLYH  120
IGYFGGIFFI ILLTIDRYLA IVHAVFALKA RTVTFGVVTS VITWFVAVFA SVPGIIFTKS  180
QKEDSVYVCG PYFPRGWNHF HTIMRNLLGL VLPLLVMIIC YSGILKTLLR CRNEKKRHRA  240
VRLIFTIMIV YFLFWTPYNI VVLLNTFQEF FGLSNCESTS QLDQATQVTE TLGMTHCCIN  300
PIIYAFVGEK FRRYLSVFFR KHIAKRFCKQ CPVFYRETVD GVTSTNTPST GEQEVSAGL   359

SEQ ID NO: 4            moltype = AA  length = 360
FEATURE                 Location/Qualifiers
source                  1..360
                        mol_type = protein
                        organism = Macaca mulatta
SEQUENCE: 4
MLSTSRSRFI RNTNGSGEEV TTFFDYDYGA PCHKFDVKQI GAQLLPPLYS LVFIFGFVGN   60
MLVVLILINC KKLKSLTDIY LLNLAISDLL FLITLPLWAH SAANEWVFGN AMCKLFTGLY  120
HIGYLGGIFF IILLTIDRYL AIVHAVFALK ARTVTFGVVT SVITWLVAVF ASVPGIIFTK  180
```

```
CQEEDSVYIC GPYFPRGWNN FHTIMRNILG LVLPLLIMVI CYSGILKTLL RCRNEKKRHR    240
AVRLIFTIMI VYFLFWTPYN IVILLNTFQE FFGLSNCEST RQLDQATQVT ETLGMTHCCI    300
NPIIYAFVGE KFRRYLSMFF RKYITKRFCK QCPVFYRETV DGVTSTNTPS TAEQEVSVGL    360

SEQ ID NO: 5           moltype = AA   length = 99
FEATURE                Location/Qualifiers
source                 1..99
                       mol_type = protein
                       organism = Homo sapiens
SEQUENCE: 5
MKVSAALLCL LLIAATFIPQ GLAQPDAINA PVTCCYNFTN RKISVQRLAS YRRITSSKCP     60
KEAVIFKTIV AKEICADPKQ KWVQDSMDHL DKQTQTPKT                            99

SEQ ID NO: 6           moltype = AA   length = 352
FEATURE                Location/Qualifiers
source                 1..352
                       mol_type = protein
                       organism = Homo sapiens
SEQUENCE: 6
MDYQVSSPIY DINYYTSEPC QKINVKQIAA RLLPPLYSLV FIFGFVGNML VILILINCKR     60
LKSMTDIYLL NLAISDLFFL LTVPFWAHYA AAQWDFGNTM CQLLTGLYFI GFFSGIFFII    120
LLTIDRYLAV VHAVFALKAR TVTFGVVTSV ITWVVAVFAS LPGIIFTRSQ KEGLHYTCSS    180
HFPYSQYQFW KNFQTLKIVI LGLVLPLLVM VICYSGILKT LLRCRNEKKR HRAVRLIFTI    240
MIVYFLFWAP YNIVLLLNTF QEFFGLNNCS SSNRLDQAMQ VTETLGMTHC CINPIIYAFV    300
GEKFRNYLLV FFQKHIAKRF CKCCSIFQQE APERASSVYT RSTGEQEISV GL            352

SEQ ID NO: 7           moltype = AA   length = 360
FEATURE                Location/Qualifiers
source                 1..360
                       mol_type = protein
                       organism = synthetic construct
SEQUENCE: 7
MLSTSRSRFI RNTNESGEEV TTFFDYDYGA PCHKFDVKQI GAQLLPPLYS LVFIFGFVGN     60
MLVVLILINC KKLKCLTDIY LLNLAISDLL FLITLPLWAH SAANEWVFGN AMCKLFTGLY    120
HIGYFGGIFF IILLTIDRYL AIVHAVFALK ARTVTFGVVT SVITWLVAVF ASVPGIIFTK    180
CQEEDSVYIC GPYFPRGWNN FHTIMRNILG LVLPLLIMVI CYSGILKTLL RCRNEKKRHR    240
AVRVIFTIMI VYFLFWTPYN IVILLNTFQE FFGLSNCEST SQLDQATQVT ETLGMTHCCI    300
NPIIYAFVGE KFRRYLSVFF RKHITKRFCK QCPVFYRETV DGVTSTNTPS TGEQEVSAGL    360

SEQ ID NO: 8           moltype = AA   length = 360
FEATURE                Location/Qualifiers
source                 1..360
                       mol_type = protein
                       organism = synthetic construct
SEQUENCE: 8
MLSTSRSRFI RNTNESGEEV TTFFDYDYGA PCHKFDVKQI GAQLLPPLYS LVFIFGFVGN     60
MLVVLILINC KKLKCLTDIY LLNLAISDLL FLITLPLWAH SAANEWVFGN AMCKLFTGLY    120
HIGYFGGIFF IILLTIDRYL AIVHAVFALK ARTVTFGVVT SVITWLVAVF ASVPGIIFTK    180
CQKEDSVYVC GPYFPRGWNN FHTIMRNILG LVLPLLIMVI CYSGILKTLL RCRNEKKRHR    240
AVRVIFTIMI VYFLFWTPYN IVILLNTFQE FFGLSNCEST RQLDQATQVT ETLGMTHCCI    300
NPIIYAFVGE KFRRYLSVFF RKHITKRFCK QCPVFYRETV DGVTSTNTPS TGEQEVSAGL    360

SEQ ID NO: 9           moltype = AA   length = 360
FEATURE                Location/Qualifiers
source                 1..360
                       mol_type = protein
                       organism = synthetic construct
SEQUENCE: 9
MLSTSRSRFI RNTNGSGEEV TTFFDYDYGA PCHKFDVKQI GAQLLPPLYS LVFIFGFVGN     60
MLVVLILINC KKLKCLTDIY LLNLAISDLL FLITLPLWAH SAANEWVFGN AMCKLFTGLY    120
HIGYFGGIFF IILLTIDRYL AIVHAVFALK ARTVTFGVVT SVITWLVAVF ASVPGIIFTK    180
CQKEDSVYVC GPYFPRGWNN FHTIMRNILG LVLPLLIMVI CYSGILKTLL RCRNEKKRHR    240
AVRVIFTIMI VYFLFWTPYN IVILLNTFQE FFGLSNCEST SQLDQATQVT ETLGMTHCCI    300
NPIIYAFVGE KFRRYLSVFF RKHITKRFCK QCPVFYRETV DGVTSTNTPS TGEQEVSAGL    360

SEQ ID NO: 10          moltype = AA   length = 5
FEATURE                Location/Qualifiers
source                 1..5
                       mol_type = protein
                       organism = synthetic construct
SEQUENCE: 10
RYTMH                                                                  5

SEQ ID NO: 11          moltype = AA   length = 17
FEATURE                Location/Qualifiers
source                 1..17
                       mol_type = protein
                       organism = synthetic construct
```

-continued

| | | |
|---|---|---|
| SEQUENCE: 11 FIVPSTGYTK YNQKFKD | | 17 |
| SEQ ID NO: 12 FEATURE source | moltype = AA  length = 9 Location/Qualifiers 1..9 mol_type = protein organism = synthetic construct | |
| SEQUENCE: 12 NKEVDYGAS | | 9 |
| SEQ ID NO: 13 FEATURE source | moltype = AA  length = 16 Location/Qualifiers 1..16 mol_type = protein organism = synthetic construct | |
| SEQUENCE: 13 KSSQSLLDSD GRTYLN | | 16 |
| SEQ ID NO: 14 FEATURE source | moltype = AA  length = 7 Location/Qualifiers 1..7 mol_type = protein organism = synthetic construct | |
| SEQUENCE: 14 LVSKLDS | | 7 |
| SEQ ID NO: 15 FEATURE source | moltype = AA  length = 9 Location/Qualifiers 1..9 mol_type = protein organism = synthetic construct | |
| SEQUENCE: 15 WQGSHFPQT | | 9 |
| SEQ ID NO: 16 FEATURE source | moltype = AA  length = 8 Location/Qualifiers 1..8 mol_type = protein organism = synthetic construct | |
| SEQUENCE: 16 GSTFTRYT | | 8 |
| SEQ ID NO: 17 FEATURE source | moltype = AA  length = 8 Location/Qualifiers 1..8 mol_type = protein organism = synthetic construct | |
| SEQUENCE: 17 IVPSTGYT | | 8 |
| SEQ ID NO: 18 FEATURE source | moltype = AA  length = 11 Location/Qualifiers 1..11 mol_type = protein organism = synthetic construct | |
| SEQUENCE: 18 ARNKEVDYGA S | | 11 |
| SEQ ID NO: 19 FEATURE source | moltype = AA  length = 11 Location/Qualifiers 1..11 mol_type = protein organism = synthetic construct | |
| SEQUENCE: 19 QSLLDSDGRT Y | | 11 |
| SEQ ID NO: 20 SEQUENCE: 20 000 | moltype =    length = | |
| SEQ ID NO: 21 FEATURE source | moltype = AA  length = 9 Location/Qualifiers 1..9 mol_type = protein organism = synthetic construct | |
| SEQUENCE: 21 WQGSHFPQT | | 9 |

```
SEQ ID NO: 22             moltype = AA    length = 118
FEATURE                   Location/Qualifiers
source                    1..118
                          mol_type = protein
                          organism = synthetic construct
SEQUENCE: 22
QVQLVQSGAE VKKPGASVKV SCKASGSTFT RYTMHWVRQA PGQRLEWIGF IVPSTGYTKY   60
NQKFKDRVTI TRDTSASTAY MELSSLRSED TAVYYCARNK EVDYGASWGQ GTLVTVSS   118

SEQ ID NO: 23             moltype = AA    length = 112
FEATURE                   Location/Qualifiers
source                    1..112
                          mol_type = protein
                          organism = synthetic construct
SEQUENCE: 23
DVVMTQSPLS LPVTLGQPAS ISCKSSQSLL DSDGRTYLNW FQQRPGQSPR RLIYLVSKLD   60
SGVPDRFSGS GSGTDFTLKI TRVEAEDVGV YYCWQGSHFP QTFGQGTKVE IK         112

SEQ ID NO: 24             moltype = AA    length = 137
FEATURE                   Location/Qualifiers
source                    1..137
                          mol_type = protein
                          organism = synthetic construct
SEQUENCE: 24
MERHWIFLLL LSVTAGVHSQ VHLQQSGTEL ARPGASIKLS CKTSGSTFTR YTMHWIKQRP   60
GQGLEWIGFI VPSTGYTKYN QKFKDKATLT ADKSSSTAYM HLNSLTSEDS ALYYCARNKE 120
VDYGASWGQG TLVTVSA                                                137

SEQ ID NO: 25             moltype = AA    length = 133
FEATURE                   Location/Qualifiers
source                    1..133
                          mol_type = protein
                          organism = synthetic construct
SEQUENCE: 25
MSPAQFLFLL VLWIRVSEIN GDVVMTQSPL TLSVTIGQPA SISCKSSQSL LDSDGRTYLN   60
WLLQRPGQSP KRLIYLVSKL DSGVPDRFTG SGSGTDFTLK ISRVEAEDLG LYYCWQGSHF 120
PQTFGGGTKL EIK                                                    133

SEQ ID NO: 26             moltype = AA    length = 98
FEATURE                   Location/Qualifiers
source                    1..98
                          mol_type = protein
                          organism = Homo sapiens
SEQUENCE: 26
QVQLVQSGAE VKKPGASVKV SCKASGYTFT SYAMHWVRQA PGQRLEWMGW INAGNGNTKY   60
SQKFQGRVTI TRDTSASTAY MELSSLRSED TAVYYCAR                          98

SEQ ID NO: 27             moltype = AA    length = 100
FEATURE                   Location/Qualifiers
source                    1..100
                          mol_type = protein
                          organism = Homo sapiens
SEQUENCE: 27
DVVMTQSPLS LPVTLGQPAS ISCRSSQSLV YSDGNTYLNW FQQRPGQSPR RLIYKVSNRD   60
SGVPDRFSGS GSGTDFTLKI SRVEAEDVGV YYCMQGTHWP                        100

SEQ ID NO: 28             moltype = AA    length = 118
FEATURE                   Location/Qualifiers
source                    1..118
                          mol_type = protein
                          organism = synthetic construct
SEQUENCE: 28
EVQLVESGGG LVKPGGSLKL SCVASGFTLS NYAMSWVRQS PEKRLEWVAE VSSSGIYIYY   60
SDTVTGRFSI SRDNAKNTLY LEMSSLRSED TAIYYCARDR YAYAMDYWGH GTSVIVSS   118

SEQ ID NO: 29             moltype = AA    length = 113
FEATURE                   Location/Qualifiers
source                    1..113
                          mol_type = protein
                          organism = synthetic construct
SEQUENCE: 29
DIVMTQSPSS LAISVGQRVT LSCKSSQSLL NSYNQKNSLA WYQQKPGQSP KLLVYFASTR   60
ESGVPDRFIG SGSGTYFTLT ITSVQAGDLA DYFCQQHYSN PRTFGGGTRL EIK        113
```